(12) United States Patent
Elf et al.

(10) Patent No.: US 10,041,104 B2
(45) Date of Patent: Aug. 7, 2018

(54) MICROFLUIDIC DEVICE

(71) Applicant: Johan Elf, Uppsala (SE)

(72) Inventors: Johan Elf, Uppsala (SE); Özden Baltekin, Uppsala (SE); Dan I. Andersson, Uppsala (SE)

(73) Assignee: Astrego Diagnostics AB, Uppsala (SE)

( * ) Notice: Subject to any disclaimer, the term of this patent is extended or adjusted under 35 U.S.C. 154(b) by 39 days.

(21) Appl. No.: 15/323,357

(22) PCT Filed: Jun. 12, 2015

(86) PCT No.: PCT/SE2015/050685
§ 371 (c)(1),
(2) Date: Dec. 30, 2016

(87) PCT Pub. No.: WO2016/007068
PCT Pub. Date: Jan. 14, 2016

(65) Prior Publication Data
US 2017/0137861 A1    May 18, 2017

Related U.S. Application Data

(63) Continuation-in-part of application No. PCT/SE2015/050227, filed on Feb. 27, 2015.

(30) Foreign Application Priority Data

Jul. 7, 2014  (SE) ..................... 1450860

(51) Int. Cl.
| | | |
|---|---|---|
| *C12M 1/34* | (2006.01) | |
| *B01L 3/00* | (2006.01) | |
| *C12Q 1/18* | (2006.01) | |
| *C12N 15/10* | (2006.01) | |
| *C12Q 1/6874* | (2018.01) | |
| *C12Q 1/6806* | (2018.01) | |
| *G01N 33/483* | (2006.01) | |
| *C12Q 1/6841* | (2018.01) | |

(52) U.S. Cl.
CPC .......... *C12Q 1/18* (2013.01); *B01L 3/502761* (2013.01); *C12N 15/1093* (2013.01); *C12Q 1/6806* (2013.01); *C12Q 1/6841* (2013.01); *C12Q 1/6874* (2013.01); *G01N 33/4833* (2013.01)

(58) Field of Classification Search
CPC ....................................... C12Q 1/18
USPC ......................................... 506/10
See application file for complete search history.

(56) References Cited

U.S. PATENT DOCUMENTS

2013/0078163 A1   3/2013  Chung et al.
2014/0248621 A1*  9/2014  Collins .............. G01N 15/1031
                                                     435/6.12

FOREIGN PATENT DOCUMENTS

| EP | 2733199 A1    | 5/2014 |
|---|---|---|
| WO | 2011/028818 A2 | 3/2011 |
| WO | 2013/075248 A1 | 5/2013 |
| WO | 2013/115725 A1 | 8/2013 |

OTHER PUBLICATIONS

Liang Zhu et al., Filter-based microfluidic device as a platform for immunofluoriescent assay of microbial cells, Lab Chip, 4:337-341 (2004).
Ping Wang et al., Robust Growth of *Escherichia coli*, Current Biology, 20:1099-1103 (Jun. 22, 2010).
Zhicheng Long et al., Microfluidic chemostat for measuring single cell dynamics in bacteria, Lab Chip, 13:947-954 (2013).
Saurabh Vyawahare et al., In vitro microbial culture models and their application in drug development, Advanced Drug Delivery Reviews, 69-70:217-224 (online Feb. 21, 2014).
European Search Report dated May 24, 2018 from corresponding European Application No. 15818165.1.

* cited by examiner

Primary Examiner — Karla A Dines
(74) Attorney, Agent, or Firm — Porter, Wright, Morris and Arthur, LLP

(57) ABSTRACT

A microfluidic device (1) comprises a substrate (10) transparent for imaging and having a plurality of spatially defined and separated cell channels (20) having a dimension to accommodate cells in monolayer. A respective first end (22) of the cell channels(20) is in fluid connection with a flow input channel (30) having a first end (32) in fluid connection with a first fluid port (31) and a second end (34) in fluid connection with a second fluid port (33). A respective second end (24) of the cell channels (20) is in fluid connection with a first end (42) of a respective wash channel (40) having a second end (44) in fluid connection with a flow output channel (50). The flow output channel (50) is in fluid connection with a third fluid port (51). The wash channels (40) have a dimension too small to accommodate the cells.

14 Claims, 14 Drawing Sheets

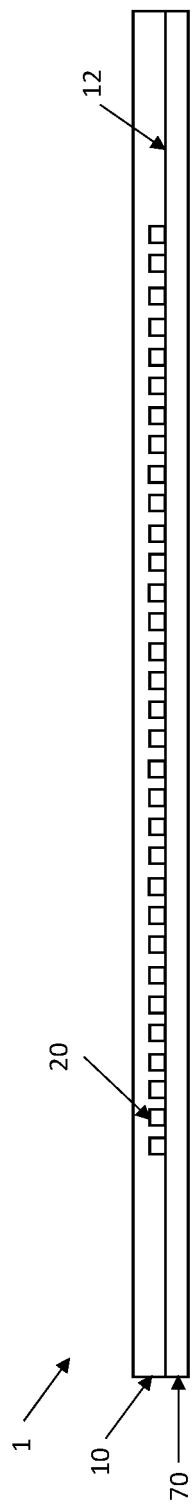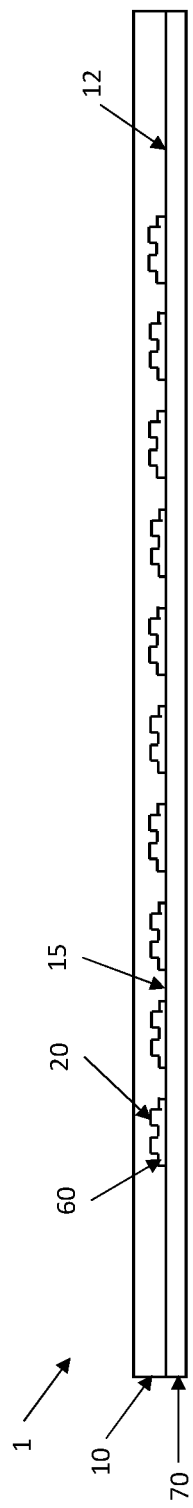

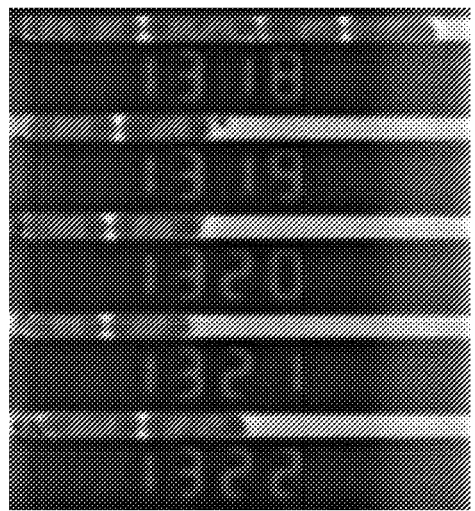
Time = t
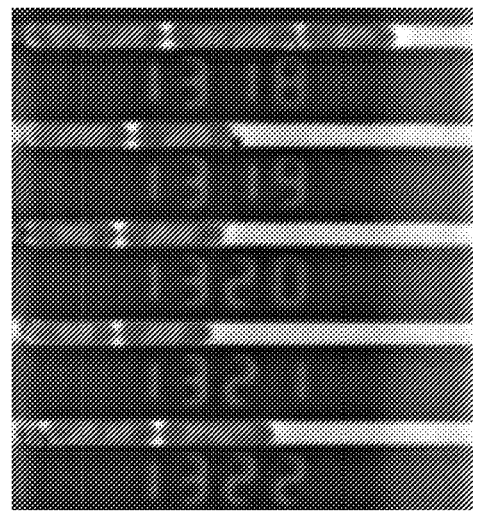
Time = t+15min
Nonresistent strain
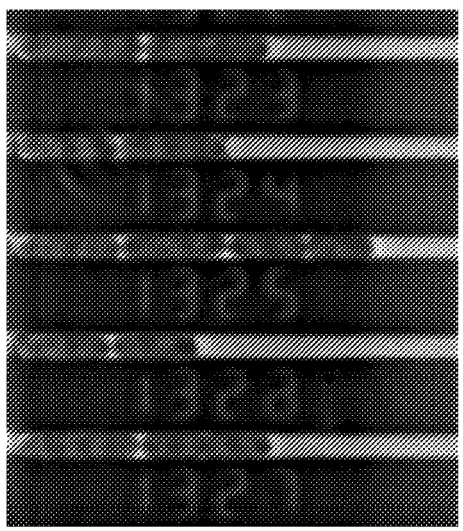
Time = t
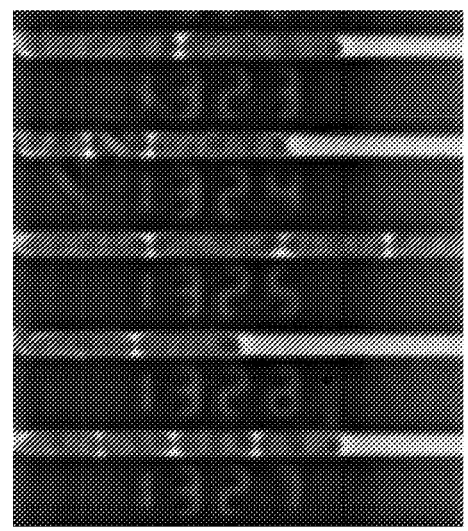
Time = t+15min
Resistent strain
Fig. 15

MICROFLUIDIC DEVICE

TECHNICAL FIELD

The present embodiments generally relate to microfluidic devices, and in particular to such microfluidic devices configured for culturing and monitoring cells.

BACKGROUND

The recent development in single cell biology has made it clear that isogenic cells can display large differences in gene expression and behavior also when grown under identical conditions. New devices are thereby needed to characterize cell to cell differences in phenotypes over time. Such devices need to meet certain criteria in order to be an effective tool in culturing and monitoring single cells. For instance, these devices should be easy to load with cells so that one can monitor phenotypic characteristics immediately after loading. Furthermore, many different individual cells need to be grown in parallel to characterize the cell-to-cell differences. The devices should be designed to enable culturing of cells for a long period of time under constant and well-controlled growth conditions to monitor, for example, linage dependent dynamics. It is further preferred if the devices enable change of culturing conditions to monitor dynamic changes in response to new culture media or test agents. For instance, it could be advantageous to test different culture media on isogenic cells in parallel or monitor the response to media changes on different cell strains in parallel.

A desired application of microfluidic devices is to rapidly and in parallel monitor the phenotypic response of a bacterial sample to a set of antibiotics or other test agents immediately after the bacterial cells have been loaded in the microfluidic device. In such an application, it would be advantageous to be able to directly load the microfluidic device with, for example, urine samples with bacteria or bacteria mixed with blood cells to gain speed in the analysis.

Another desired application, which can be combined with antibiotic susceptibility testing (AST), would be to probe the genetic variability in a cell sample by first monitoring the phenotypic characteristics and then determining genotypic characteristics.

A prior art microfluidic device, denoted the "Mother Machine", is disclosed in Wang et al., *Current Biology* 2010, 20: 1099-1103. . The Mother Machine allows for monitoring cells in many different cell channels in parallel. However, this prior art microfluidic device has several shortcomings. For instance, cell loading is complicated and it is hard to rapidly change culture conditions in the microfluidic device.

There is therefore a need for an improved microfluidic device that overcomes some or all of the shortcomings of prior art microfluidic devices.

SUMMARY

It is an objective of the embodiments to provide an improved microfluidic device.

This and other objectives are met by embodiments as disclosed herein.

An aspect of the embodiments relates to a microfluidic device comprising a substrate transparent for imaging and having a plurality of spatially defined and separated cell channels having a dimension to accommodate cells in monolayer. A respective first end of the plurality of spatially defined and separated cell channels is in fluid connection with a flow input channel having a first end in fluid connection with a first fluid port and a second end in fluid connection with a second fluid port. A respective second end of the plurality of spatially defined and separated cell channels is in fluid connection with a first end of a respective first wash channel having a second end in fluid connection with a flow output channel. The flow output channel is in fluid connection with a third fluid port. The first wash channels have a dimension too small to accommodate the cells.

Another aspect of the embodiments relates to a method of loading a microfluidic device according to above. The method comprises inputting cells and culture medium in one of a first fluid port and a second fluid port of the microfluidic device to allow the cells and culture medium to flow through a flow input channel of the microfluidic device and into a plurality of spatially defined and separated cell channels. A respective first end of the plurality of spatially defined and separated cell channels is in fluid connection with the flow input channel having a first end in fluid connection with the first fluid port and a second end in fluid connection with the second fluid port. The method also comprises outputting excessive cells through the other of the first fluid port and the second fluid port and outputting culture medium through the other of the first fluid port and the second fluid port and through a third port in fluid connection with a flow output channel. A respective second end of the plurality of spatially defined and separated cell channels is in fluid connection with a first end of a respective first wash channel having a second end in fluid connection with the flow output channel. The first wash channels have a dimension too small to accommodate the cells.

A further aspect of the embodiments relates to a method for antibiotic susceptibility testing. The method comprises loading bacteria cells into a plurality of spatially defined and separated cell channels of a microfluidic device according to above. The method also comprises exposing bacteria cells in different spatially defined and separated cell channels of the plurality of spatially defined and separated cell channels to different antibiotics and/or to different concentrations of an antibiotic. The method further comprises determining antibiotic susceptibility of the bacteria cells based on a respective phenotype characteristic, preferably at least one of a respective growth rate, a respective degree of nucleoid compaction, a respective degree of metabolic activity and a respective degree of membrane integrity, of the bacteria cells in the plurality of spatially defined and separated cell channels.

Yet another aspect of the embodiments relates to a method for in situ genotyping cells. The method comprises loading cells into a plurality of spatially defined and separated cell channels of a microfluidic device according to above. The method also comprises fixating the cells in the plurality of spatially defined and separated cell channels and in situ genotyping the cells in the plurality of the spatially defined and separated cell channels.

A further aspect of the embodiments relates to a method for phenotype characterization of cells. The method comprises loading cells into a plurality of spatially defined and separated cell channels of a microfluidic device according to above. The method also comprises growing the cells in the plurality of spatially defined and separated cell channels and real-time monitoring a phenotype characteristic of the cells in the plurality of spatially defined and separated cell channels.

The microfluidic device of the embodiments is easy to load with cells and enables culturing cells under constant or variable conditions. The microfluidic device enables rapid switches of culturing conditions or application of chemicals, reagents or other agents.

BRIEF DESCRIPTION OF THE DRAWINGS

The embodiments, together with further objects and advantages thereof, may best be understood by making reference to the following description taken together with the accompanying drawings, in which:

FIG. 2 is a cross-sectional view of the microfluidic device shown in FIG. 1 along the line A-A;

FIG. 4 is a cross-sectional view of the microfluidic device shown in FIG. 3 along the line A-A;

FIG. 15 illustrates phase contrast images of chloramphenicol-susceptible (MIC≈4 µg/ml) chloramphenicol-resistant (MIC>12 µg/ml) *E. coli* strains growing in a microfluidic device according to an embodiment;

DETAILED DESCRIPTION

Throughout the drawings, the same reference numbers are used for similar or corresponding elements.

The present embodiments generally relate to microfluidic devices, and in particular to such microfluidic devices configured for culturing and monitoring cells.

The microfluidic device of the embodiments facilitates long term cell culturing under constant or variable conditions. The microfluidic device is easily loaded with cells and enables rapid switches of growth conditions and addition or exchange of biological or chemical agents.

The microfluidic device of the embodiments can be used for single cell culturing and experiments. In such applications, individual cells are kept separated from other cells in an input sample. For instance, the microfluidic device can be used to keep and culture cells of a respective cell strain in a library of multiple cell strains separately from cells of other cell strains. Hence, each cell strain has then a respectively spatially defined and separated cell channel in the microfluidic device in which the cells can grow and be studied.

An aspect of the embodiments relates to a microfluidic device, also referred to as culturing device. The microfluidic device comprises a substrate transparent for imaging and having a plurality of spatially defined and separated cell channels having a dimension to accommodate cells in monolayer. A respective first end of the plurality of spatially defined and separated cell channels is in fluid connection with a flow input channel, also referred to as flow channel. The flow input channel has a first end in fluid connection with a first fluid port, also referred to as fluid source, and a second end in fluid connection with a second fluid port, also referred to as fluid sink. A respective second end of the plurality of spatially defined and separated cell channels is in fluid connection with a first end of a respective first wash channel having a second end in fluid connection with a flow output channel, also referred to as sink channel. The flow output channel is in fluid connection with a third fluid port, also referred to as wash sink. The first wash channels have a dimension too small to accommodate the cells.

Various implementation embodiments of the microfluidic device will now be further described with reference to the drawings.

Figure 1:
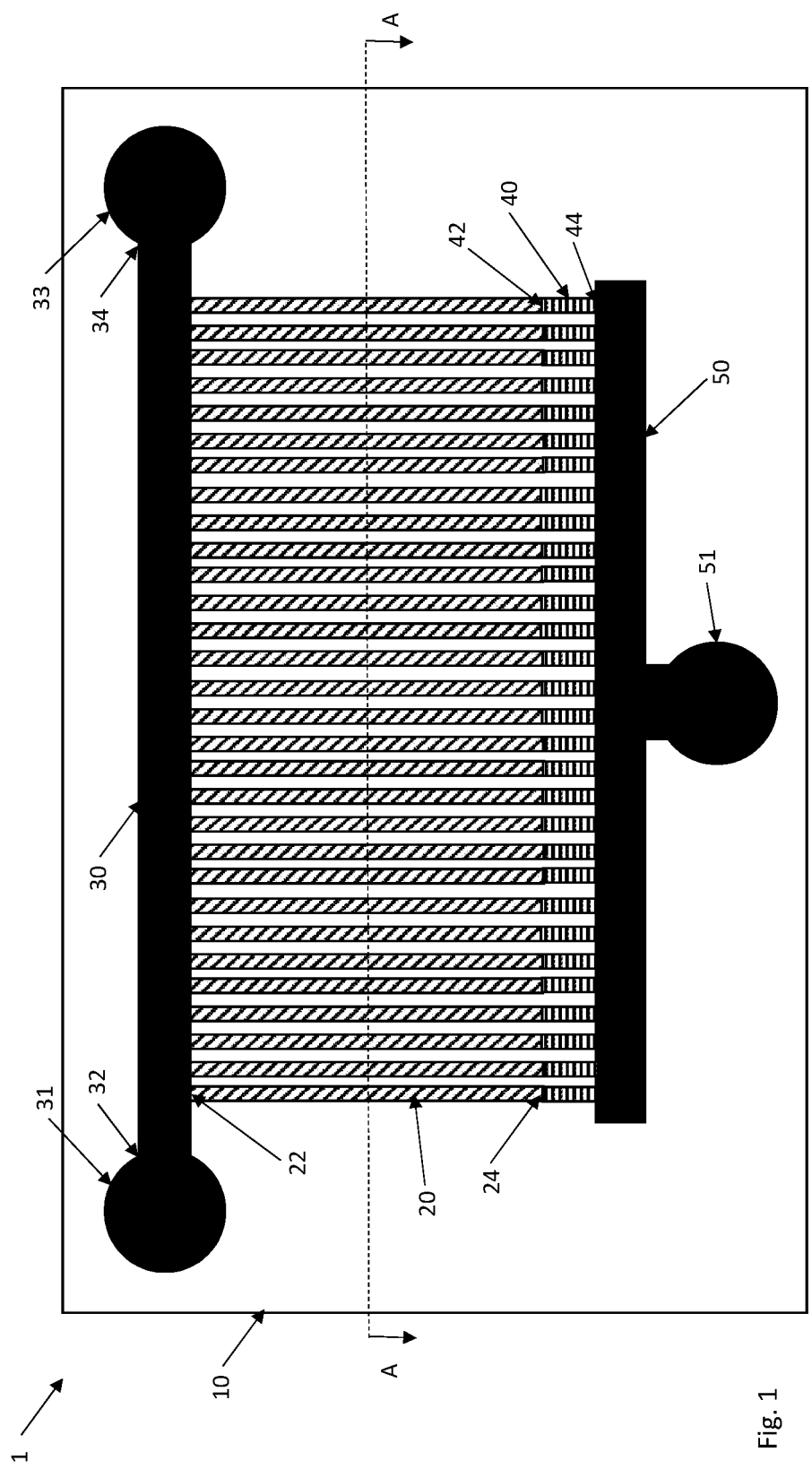
FIG. 1 is an illustration of a microfluidic device according to an embodiment.

In an embodiment, the microfluidic device 1, see FIG. 1, comprises a substrate 10 transparent for imaging and having a plurality of spatially defined and separated cell channels 20. The cell channels 20 have a dimension to accommodate cells in monolayer. A respective first end 22 of the cell channels 20 is in fluid connection with a flow input channel 30 having a first fluid port 31 in a first end 32 and a second fluid port 33 in a second end 34. The first wash channels 40 are preferably present and extend from a respective second end 24 of the cell channels 20 to a flow output channel 50. Hence, a first wash channel 40 has a first end 42 in fluid connection with a second end 24 of a cell channel 20 and a second, opposite end 44 in fluid connection with the flow output channel 50. The flow output channel 50 is in fluid connection with a third fluid port 51.

The substrate 10 has multiple cell channels 20 in which cells are cultured. The cell channels 20 may be arranged in parallel as shown in FIG. 1 and further shown in the cross-sectional view taken along the line A-A in FIG. 1 as shown in FIG. 2. In such a case, a respective first end 22 of the cell channels 20 is in fluid connection with the flow input channel 30 and extends from this flow input channel 30. In order to increase the total number of cell channels 20, the cell channels 20 may extend from either longitudinal side of the flow channel 30 thereby substantially doubling the number of cell channels 20 as compared to only having cell channels 20 on one side of the flow channel 30, see FIG. 5.

Figure 5:
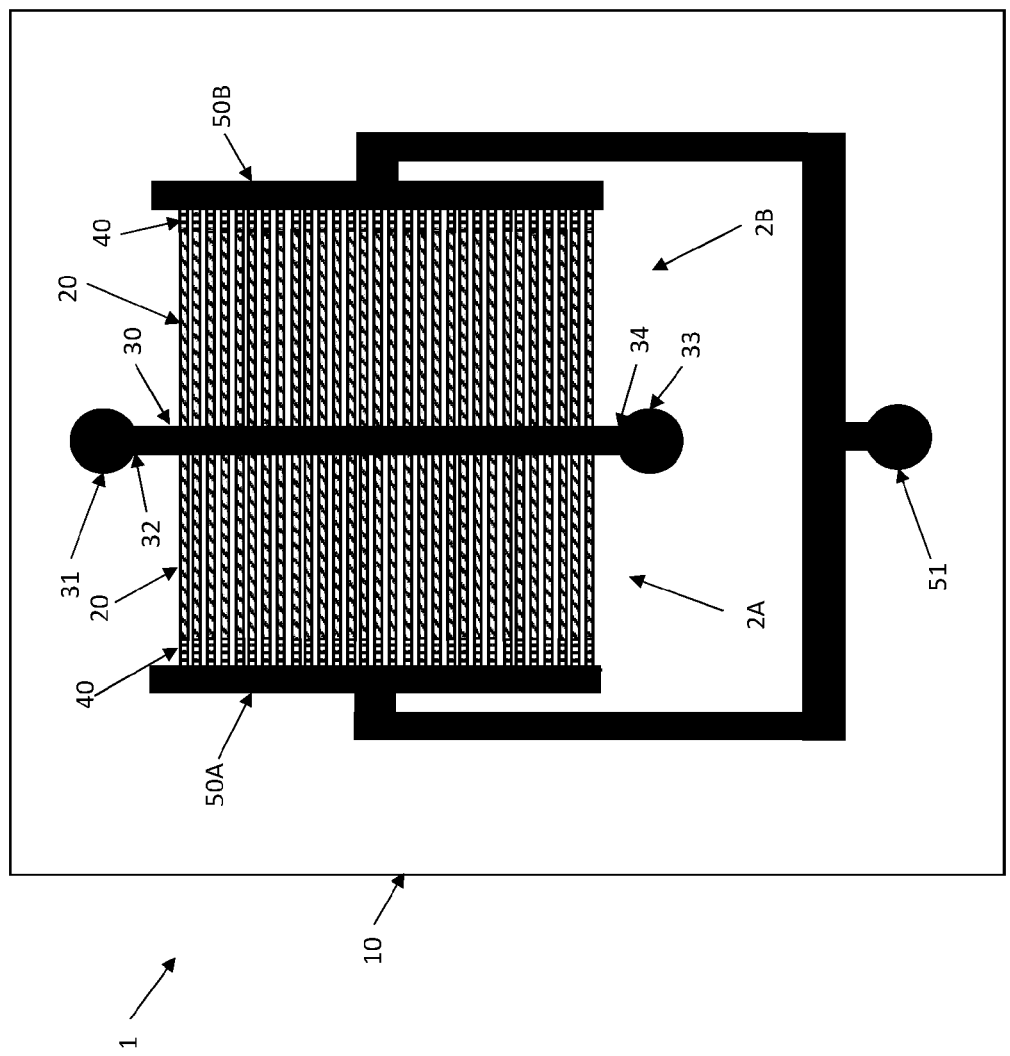
FIG. 5 is an illustration of a microfluidic device according to a further embodiment.

In the FIG. 5, the substrate 10 of the microfluidic device 1 has two sets 2A, 2B of cell channels 20. The cell channels 20 of each such set 2A, 2B have their respective first end in fluid connection to a common fluid input channel 30 with the first and second fluid ports 31, 33 in its two ends 32, 34. Each set 2A, 2B, however, has a respective flow output channel 50A, 50B as shown in FIG. 5. Hence, the second ends of the first wash channels 40 in the first set 2A are in fluid connection with a first flow output channel 50A, whereas the second ends of the first wash channels 40 in the second 2B are in fluid connection with a second flow output channel 50B. These two flow output channels 50A, 50B preferably share a common third output port 51.

The microfluidic device 1 of FIG. 5 basically multiplexes two sets 2A, 2B as shown in FIG. 1. This means that the two sets 2A, 2B of cell channels 20 and first wash channels 40 share a common flow input channel 30 connected in its first end 32 to the first fluid port 31 and in its second end 34 to the second fluid port 33. Each set 2A, 2B of cell channels 20 and first wash channels 40 ends at a respective flow output channel 50A, 50B that are interconnected and connected to a common third fluid port 51.

The cells present in cell channels 20 in the first set 2A to the left will be exposed to the same culture medium and reagents and chemicals input at the first fluid port 31 as the cells present in the cell channels 20 in the second set 2B to the right in the figure.

Figure 6:
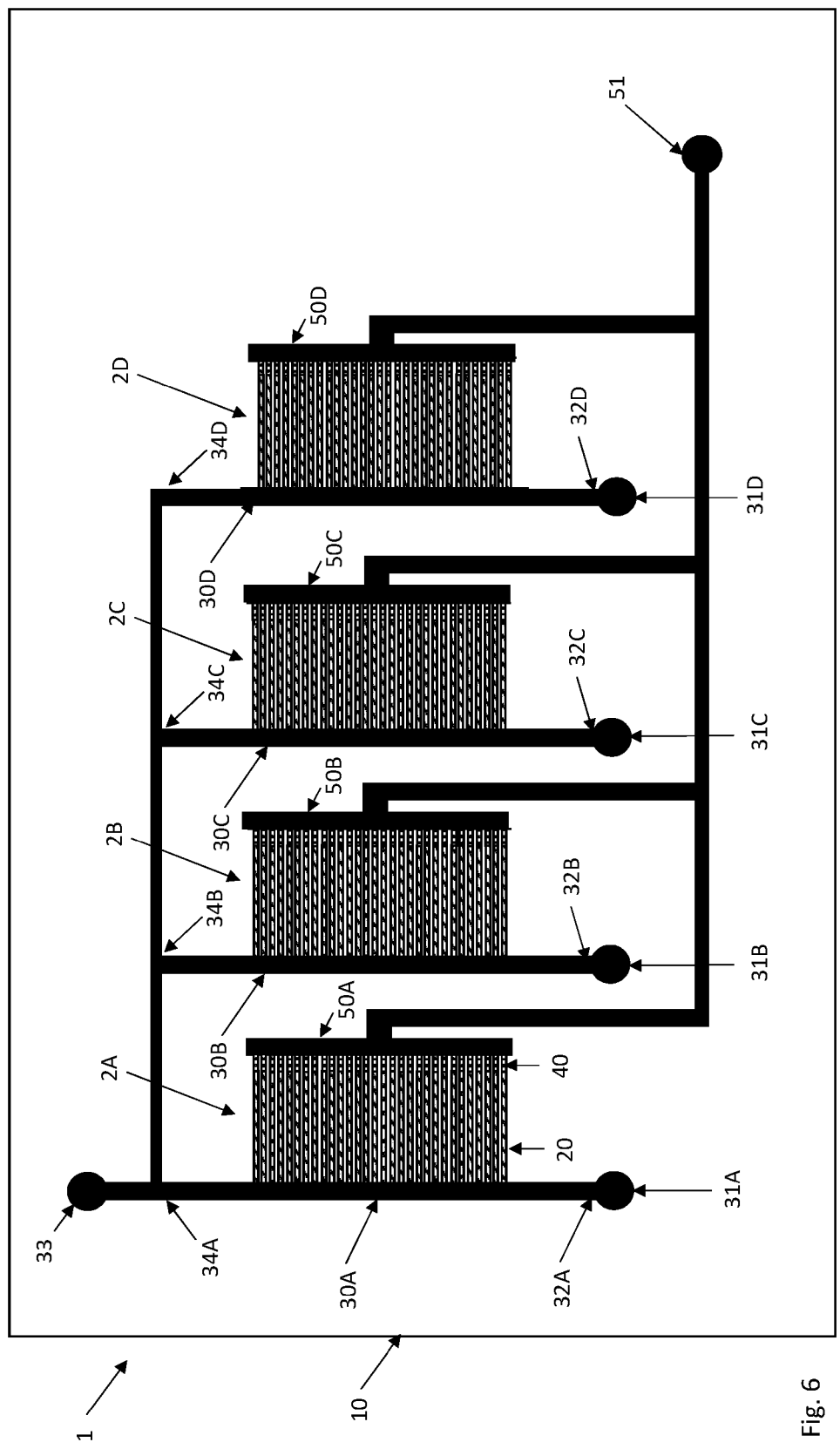
FIG. 6 is an illustration of a microfluidic device according to yet another embodiment.
Figure 7:
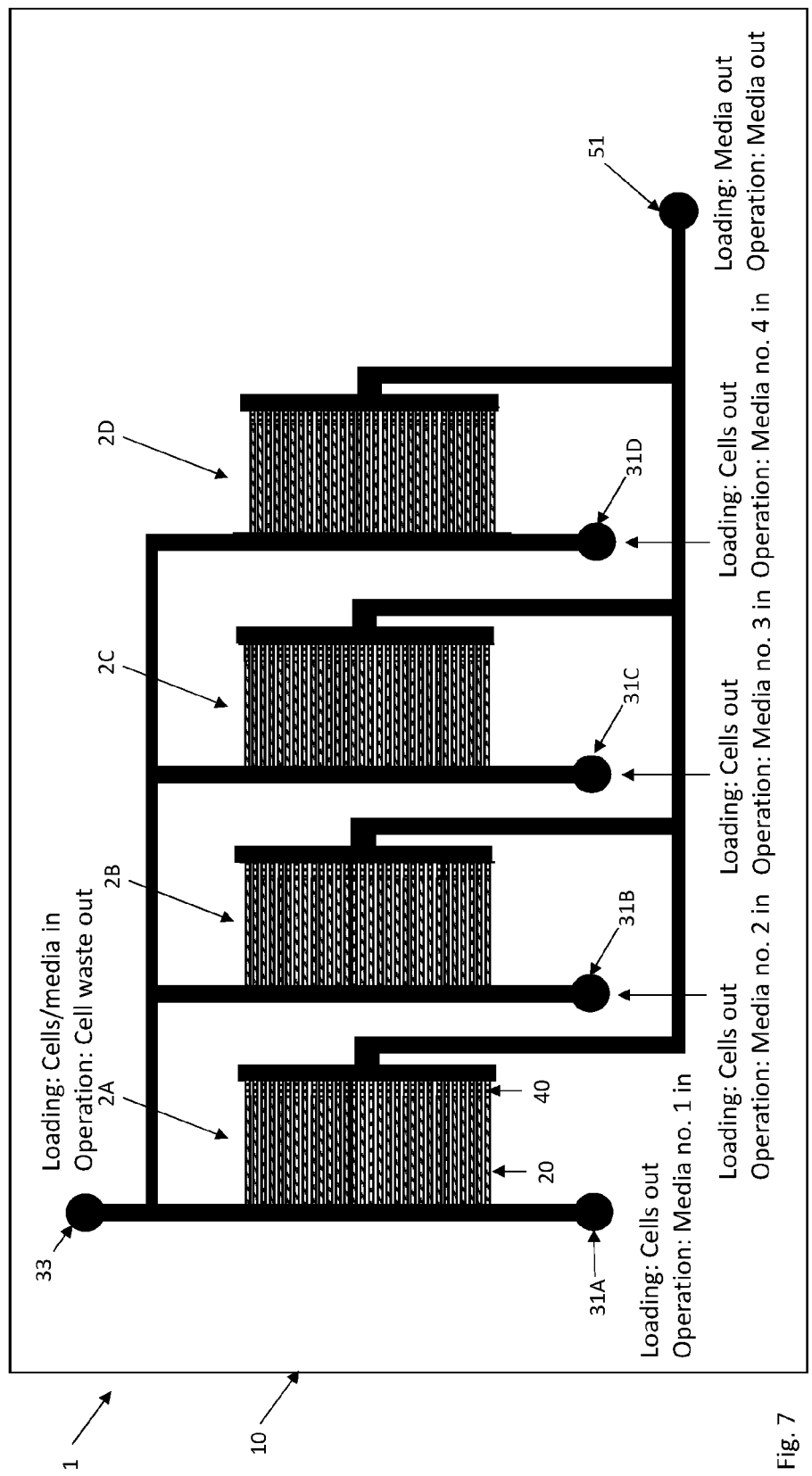
FIG. 7 is an illustration of loading and operation of the microfluidic device shown in FIG. 6.
Figure 10:
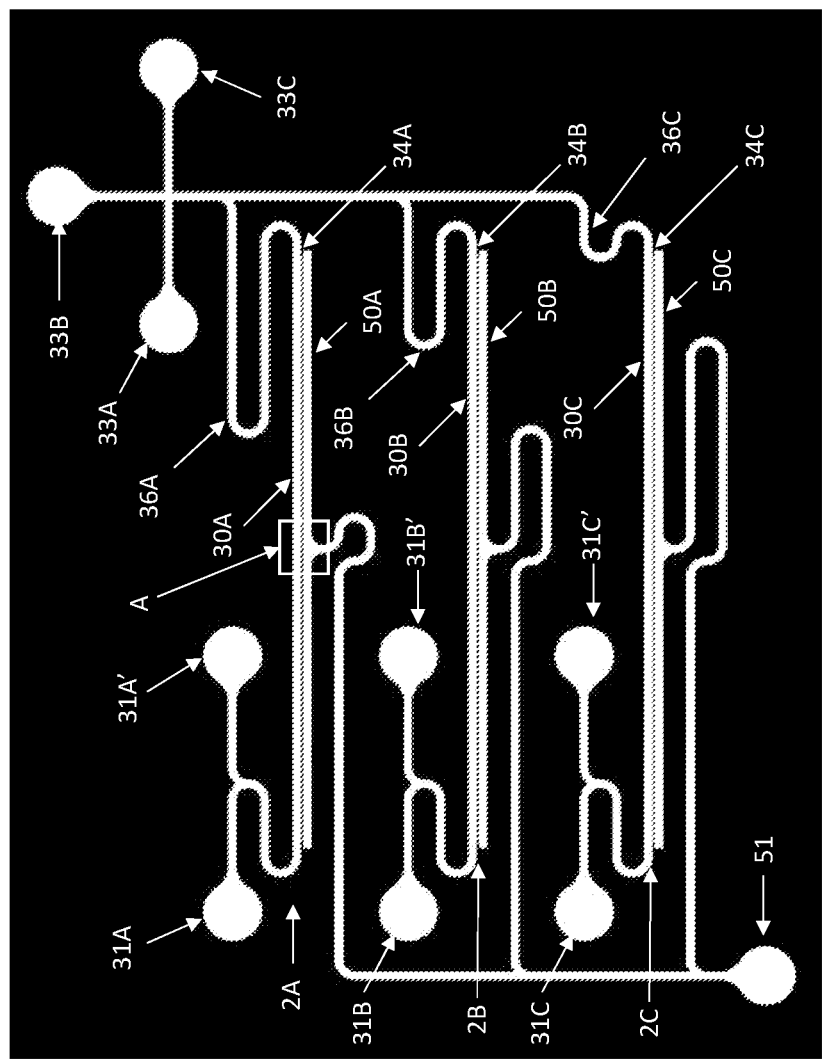
FIG. 10 is an illustration of a microfluidic device according to a further embodiment.

Also more complex arrangements of cell channels 20 and flow input channels 30 are possible in the substrate 10 as will be further described herein in connection with FIGS. 6-7 and 10. The important characteristic is that each cell channel 20 has an end 22 in fluid connection with a flow input channel 30 and that the cell channels 20 are separated to prevent cells from escaping from one cell channel 20 and entering another cell channel 20.

The cell channels 20 are dimensioned to accommodate cells in monolayer. This means that the height or diameter of the cell channels 20 is selected to be about or slightly larger than the diameter of the cells to be monitored. For instance, the cell channels 20 could be substantially quadratic in cross-section as shown in FIG. 2 with a channel side substantially matching the cell diameter of the cells. Alternatively, the cell channels 20 could have circular or U-shaped cross-section with a diameter substantially matching the cell diameter. Also other cross-sectional configurations are possible as long as the cells could be viably cultured, preferably in monolayer, in the cell channels 20. This implies that the cell channels 20 can be several cells wide but preferentially only one cell high. In this case the cells can grow in the cell channels forming a 2D monolayer that may be wider than one cell but preferably still is a monolayer.

The flow input channel 30 preferably has dimensions that are significantly larger than the diameter of the cells to be monitored. This means that any cells entering the flow input channel 30 will be flushed through the flow input channel 30 typically towards the second fluid port 33 by a, preferably continuous, flow of culture medium from the first fluid port 31 through the flow channel 30 and towards the second flow port 33. Thus, in an embodiment the flow input channel 30 has a dimension sufficient large to allow the cells to flow through the flow input channel 30.

The differences in cross-sectional dimensions of the flow input channel 30 and the cell channels 20 can further be exploited to separate cells from each other in a biological sample applied to the microfluidic device 1. For instance, the biological sample may contain cells of interest having a size sufficient small to allow the cells to enter cell channels 20 when flowing through the fluid input channel 30. The biological sample may additionally comprise larger cells that are too large to enter a cell channel 20 but still small enough to flow through the flow input channel 30. When the biological sample is input to the microfluidic device 1, such as through the first input port 31, a size separation is obtained where large cells flow past the cell channels 20 in the flow input channel 30 from the first fluid port 31 towards the second fluid port 33. However, the smaller target cells will get trapped in the cell channels 20.

If the biological sample in addition, or alternatively, comprises very small cells that have a size small enough to enter the first wash channels 40, an additional or alternative size separation is obtained. Thus, whereas the target cells enter the cell channels 20 but cannot enter the first wash channels 40 due to too large size, the very small cells will enter the cell channels 20 and flow further into the first wash channels 40 and to the flow output channel 50. These small cells will then exit the microfluidic device 1 through the third flow port 51.

Thus, large cells will never enter the cell channels 20 but are flushed through the flow input channel 30 and out through the second flow port 33. Small cells will not be retained in the cell channels 20 but rather flow through the cell channels and first wash channels 40 and further through the flow output channel 50 and the third output port 51. Accordingly, only target cells of the correct size and dimension will enter and get trapped in the cell channels 20.

The actual dimensions of the cell channels 20 and the first wash channels 40 can be selected and designed based on the particular type of cells that should be grown and monitored in the microfluidic device 1.

Generally, cells, such as of a cell strain library, are seeded by adding cells, such as cells of a respective cell strain, in each cell channel 20. The cells are thereby allowed to grow in a monolayer along the length of the cell channels 20. In an embodiment, each cell channel 20 thereby contains cells of a single cell strain and genotype. The cells in the cell channels 20 could be seen as pearls on a string if the cell channel 20 is one cell wide. If the cell channel 20 is wider the cells will form a 2D layer in the cell channel 20.

Cells growing and mitigating past the first end 22 of the cell channels 20 will enter the flow input channel 30 and are thereby flushed away. The second, opposite end 24 of the cell channels 20 is connected to the first wash channel 40, which is dimensioned to prevent cells from escaping from the second end 24 of the cell channel 20 and into the first wash channel 40.

In an embodiment, the first wash channels 40 could have a small dimension along its whole length, i.e. from the first end 42 connected to the second end 24 of a cell channel 20 to the second 44 connected to the flow output channel 50. In an alternative embodiment, the first wash channel 40 comprises a channel restriction having a dimension that is too small or narrow for cells present in a cell channel 20 to grow or flow past the channel restriction and into the first wash channel 40. This channel restriction is then present at the first end 42 of the first wash channel 40. The remaining portion of the first wash channel 40 may in this embodiment have a dimension substantially the same as the cell channels 20. The channel restriction is therefore an efficient block or obstruction for the cells but allows culture medium and any chemicals, reagents or agents to flow through the channel obstruction and further into the first wash channel 40 and the flow output channel 50.

Both these example embodiments achieve the desired effect of preventing cells of target size present in cell channels 20 to grow or flow past the second end 24 of the cell channels 20 and into the first wash channels 40.

Figure 3:
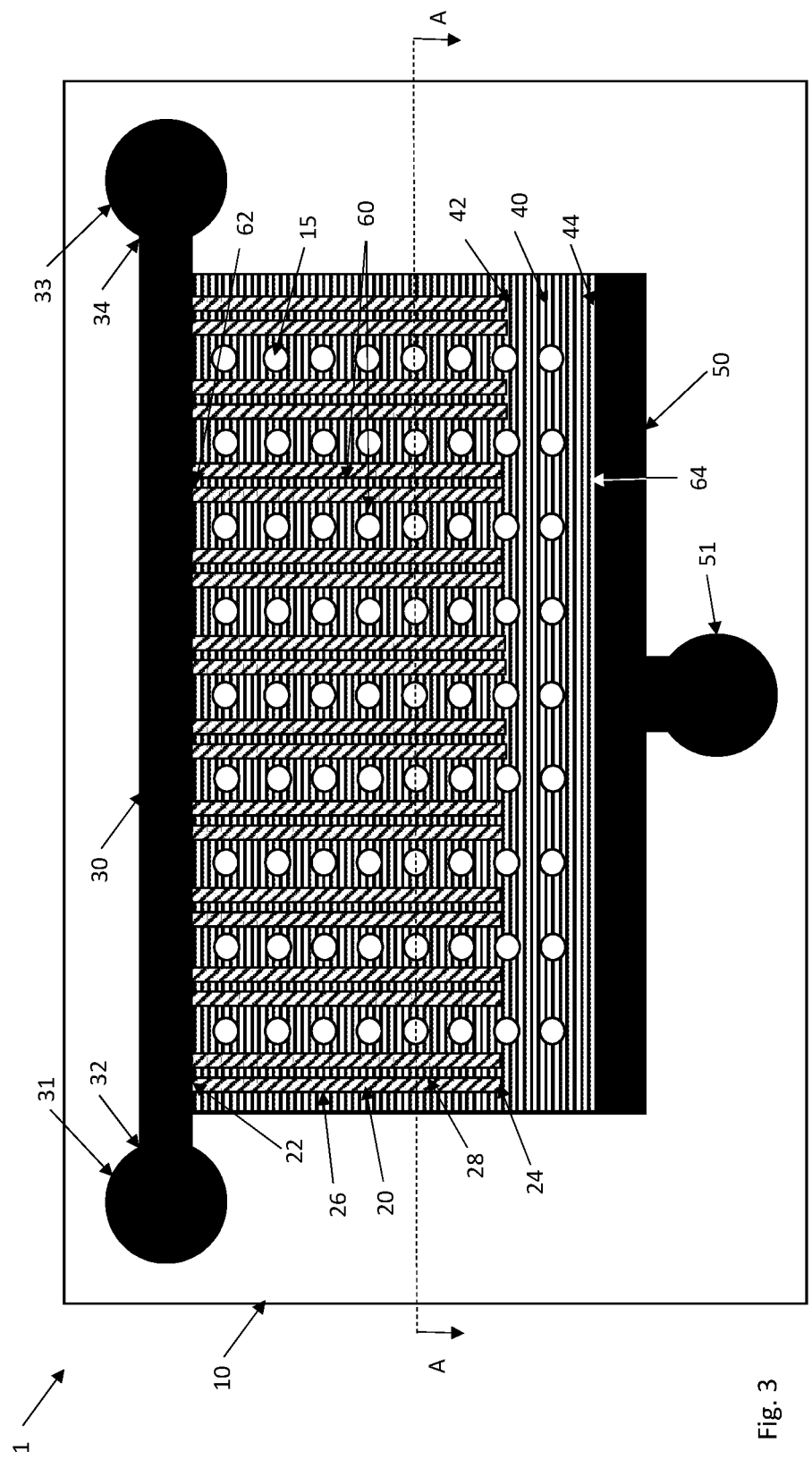
FIG. 3 is an illustration of a microfluidic device according to another embodiment.

In an embodiment, see FIG. 3, each cell channel 20 of the plurality of spatially defined and separated cell channels 20 is flanked along at least one of its longitudinal sides 26, 28 with a respective second wash channel 60 having a first end 62 in fluid connection with the flow input channel 30 and a second end 64 in fluid connection with the flow output channel 50. The second wash channels 60 have a dimension too small to accommodate the cells.

In this embodiment, each cell channel 20 has at least one second wash channel 60 in fluid connection with the cell channel 20 and arranged along one of its longitudinal sides 26, 28. The embodiment as shown FIG. 3 has second wash channels 60 arranged along both longitudinal sides 26, 28 of each cell channel 20.

In an embodiment, the first wash channels 40 and the second wash channels 60 may be interconnected, thereby forming a continuous wash layer around the cell channels 20 as shown in FIG. 3. Thus, the portion of the second wash channels 60 from the second end 24 of the cell channels 20 to the second end 64 of the second wash channels 60 may be interconnected to adjacent first wash channels 40.

The dimension of the second wash channels 60 (or wash layer), such as depth or height, is too small to accommodate cells. This means that cells present in the cell channels 20 cannot enter the adjacent second wash channels 60 but will remain in the cell channels 20.

FIG. 4 is a cross-sectional view of the microfluidic device 1 in FIG. 3 along the line A-A. This figure clearly illustrates the comparatively smaller depth of the second wash channels 60 as compared to the cell channels 20. The second wash channels 60 may have any cross-sectional configuration, such as quadratic, rectangular, circular, U-shaped, etc.

In a particular embodiment, the first and wash channels 40, 60 have a same depth in the substrate 10.

The cell channel 20 preferably has a substantially same depth when traveling from its first end 22 at the flow input channel 30 to its second end 24. This depth preferably corresponds to or is slightly larger than the cell diameter to allow cells in a monolayer in the cell channel 20. At the second end 24 of the cell channel 20 the depth will be shallower when entering the first wash channel 40 extending from the second end 24 of the cell channel 20 to the flow output channel 50. This shallower depth, which preferably is 20 smaller than the cell diameter, prevents cells present in the cell channel 20 from entering the first wash channel 40.

In an embodiment as shown in FIGS. 3 and 4, the substrate 10 preferably comprises structures 15 or portions 15 extending through the whole thickness of the substrate 10 in order to increase its stability. FIGS. 3 and 4 illustrate such structures 15 in the form of pillars provided in between some of the second wash channels 60 along the longitudinal lengths of the cell channels 20. These pillars 15 can have any shape as long as they support the wash layer and enable fluid flow. They could, for example, be rectangular, star shaped, round or triangular and positioned regularly or irregularly. These structures 15 could be separate structures as shown in the figures to promote fluid flow throughout the whole wash layer, i.e. in between second wash channels 60. In an alternative approach, each column of pillars shown in the figures forms a single structure extending over the whole length between the flow input channel 30 and the flow output channel 50. Such a solution may result in a more stable substrate 10, however, at the cost of less efficient fluid flow.

The cell channels 20 and the first and second wash channels 40, 60 are preferably open channels as shown in FIGS. 2 and 4. This means that a cover plate 70 is preferably positioned on the substrate 10 to form a lid for and seal the cell channels 20 and the first and second wash channels 40, 60. The cover plate 70 is thereby arranged onto a main surface 12 of the substrate 10.

Herein follows a short description of the operation of the microfluidic device 1.

During cell loading, the cells with culture media enter the first fluid port 31 or the second fluid port 33 and flow into the flow input channel 30. In a preferred embodiment, all fluid ports 31, 33, 51 are open to allow culture media and cells to be pushed into the cell channels 20. Excess cells, or cells that are too large to fit in the cell channels 20, are washed out through the second fluid port 33 or the first fluid port 31 as the depth of the cell channels 20 and the second wash channels 60 (if present) is too shallow to allow the cells to reach the flow output channel 50 and reach the third fluid port 51. Culture media exits the microfluidic device 1 both from the second fluid port 33 or the first fluid port 31 and the third fluid port 51. The size selection capacity of the microfluidic device 1 can be used to seed the cell channels 20 with, for instance, bacteria that are separated from, for instance, blood cells that are significantly larger.

During operation of the microfluidic device 1 culture medium enters the first fluid port 31 as described above. In a first embodiment, the second fluid port 33 and the third fluid port 51 are open. This means that culture medium will not only exit through the second fluid port 33 but also through the third fluid port 51. This means that the culture medium, test agents and reagents will effectively reach all cells within the cell channels 20. Excess cells will flow into the flow input channel 30 and further out from the second fluid port 33, whereas media flow over all the cells and into the flow output channel 50 and out from the third fluid port 51 to keep all cells supplied with fresh culture medium or reagents.

In a second embodiment, the third fluid port 51 is closed so that culture medium and excess cells both exit through the second fluid port 33. This is embodiment generally achieves a less efficient flow of cell medium over the cells in the cell channels 20 as compared to the first embodiments.

In growth, wash and reaction steps, the third fluid port 51 is preferably open. This means that the culture medium, the wash fluid or liquid and the solution with reaction reagents enters the first fluid port 31 and flows through the flow input channel 30, the cell channels 20 and the first wash channels 40 (and the optional second wash channels 60) towards the flow output channel 50 and the third fluid port 51. In another embodiment, the second fluid port 33 is open during the growth, washing and steps. In such a case, the culture medium, the wash fluid or liquid and the solution with reaction reagents may exit through the third fluid port 51 or the second fluid port 33.

FIG. 6 illustrates an embodiment of a microfluidic device 1 having multiple, i.e. at least two, sets 2A, 2B, 2C, 2D of cell channels 20 and first wash channels 40 sharing a common second fluid port 33 and third fluid port 51 but have separate, i.e. individual, first fluid ports 31A, 31B, 31C, 31D. This means that different culture media and/or reagents or chemicals can be input to cells present in one of the sets 2A of cells channels 20 as compared to cells present in another of the sets 2B, 2C, 2D of cells channels 20.

Thus, in an embodiment, the substrate 10 of the microfluidic device 1 has multiple sets 2A, 2B, 2C, 2D of the plurality of spatially defined and separated cell channels 20, multiple flow input channels 30A, 30B, 30C, 30D and multiple flow output channels 50A, 50B, 50C, 50D. The respective first end 22 of the plurality of spatially defined and separated cell channels 20 in each set 2A, 2B, 2C, 2D of the multiple sets 2A, 2B, 2C, 2D is in fluid connection with a respective flow input channel 30A, 30B, 30C, 30D of the multiple flow input channels 30A, 30B, 30C, 30D. The respective second end 44 of the first wash channels 40 in each set 2A, 2B, 2C, 2D of the multiple sets 2A, 2B, 2C, 2D is in fluid connection with a respective flow output channel 50A, 50B, 50C, 50D of the multiple flow output channels 50A, 50B, 50C, 50D.

A respective first end 32A, 32B, 32C, 32D of each flow input channel 30A, 30B, 30C, 30D of the multiple flow input channels 30A, 30B, 30C, 30D is in fluid connection with a respective first fluid port 31A, 31B, 31C, 31D. Correspondingly, a respective second end 34A, 34B, 34C, 34D of each flow input channel 30A, 30B, 30C, 30D of the multiple flow input channels 30A, 30B, 30C, 30D is in fluid connection with a common second fluid port 33. Furthermore, each flow output channel 50A, 50B, 50C, 50D of the multiple flow output channels 50A, 50B, 50C, 50D is in fluid connection with a common third fluid port 51.

The microfluidic device 1 of FIG. 6 should merely be seen as an example embodiment of having multiple, i.e. at least two, sets 2A, 2B, 2C, 2D of cell channels 20. This means that variants of the microfluidic device 1 could have a substrate with M such sets, and where M is an integer value larger than or equal to 2.

FIG. 7 schematically illustrates an embodiment of using the microfluidic device 1 of FIG. 6. In an embodiment, during loading, cells and culture medium enter the second fluid port 33 with culture medium flowing out through the third fluid port 51 and through the different first fluid ports 31A, 31B, 31C, 31D. Excessive cells flow out through the first fluid ports 31A, 31B, 31C, 31D. In another embodiment, the cells enter through the individual first fluid ports 31A, 31B, 31C, 31D with excess cells exiting through the common second port 33 and culture medium exiting through the common second fluid port 33 and the common third fluid port 51.

During operation of the microfluidic device 1, culture medium preferably enters the separate first fluid ports 31A, 31B, 31C, 31D, thereby allowing different culture medium to reach the different sets 2A, 2B, 2C, 2D of cell channels 20 and first wash channels 40. Excess cells are washed out through the common second fluid port 33 and culture medium flow out from the common third fluid port 51 and also through the common second fluid port 33.

If a same culture medium is to be used for all sets 2A, 2B, 2C, 2D of cell channels 20 and there is no need to individually add chemicals, reagents or other agents to the different sets 2A, 2B, 2C, 2D, then culture medium flow could instead be from the common second fluid port 33 and towards the common third fluid port 51 and the separate first fluid ports 31A, 31B, 31C, 31D.

FIG. 10 schematically illustrates a variant of the microfluidic device 1 described above in connection with FIGS. 6 and 7. In this embodiment the respective first end 32A, 32B, 32C of each flow input channel 30A, 30B, 30C of the multiple flow input channels 30A, 30B, 30C is in fluid connection with multiple respective first fluid ports 31A, 31A', 31B, 31B', 31C, 31C'. The respective second end 34A, 34B, 34C of each flow input channel 30A, 30B, 30C of the multiple flow input channels 30A, 30B, 30C is in fluid connection with multiple common second fluid ports 33A, 33B, 33C.

This means that in this embodiment each flow input channel 30A, 30B, 30C is in fluid connection with multiple separate first fluid ports 31A, 31A', 31B, 31B', 31C, 31C' and multiple common second fluid ports 33A, 33B, 33C. The multiple common second fluid ports 33A, 33B, 33C are thereby shared by all sets 2A, 2B, 2C of cell channels, whereas each such set 2A, 2B, 2C of cell channels has its own group of multiple first fluid ports 31A, 31A'; 31B, 31B'; 31C, 31C'.

The usage of multiple first fluid ports 31A, 31A', 31B, 31B', 31C, 31C' per set 2A, 2B, 2C of cell channels and multiple common second fluid ports 33A, 33B, 33C enable one and the same microfluidic device 1 to be operated in different modes.

A first such operation mode involves using multiple specific cell strains. In such a case, the different cell strains are loaded in the microfluidic device 1 in the first fluid ports 31A, 31B, 31C (or 31A', 31B', 31C') with at least one of the common second fluid ports 33A, 33B, 33C as exit for excess cells, whereas culture medium exit the microfluidic device 1 though the common third fluid port 51 and the open common second fluid port(s) 33A, 33B, 33C. During operation culture medium and any reagents, chemicals or agents are flown from at least one of the common second fluid ports 33A, 33B, 33C that was not used for cell waste during loading, and leaving the microfluidic device 1 through the common third fluid port 51 and the first fluid ports 31A', 31B', 31C' (or 31A, 31B, 31C).

In particular preferred embodiment, it is preferred to use one first fluid port 31A, 31B, 31C of each first fluid port pair 31A, 31A', 31B, 31B', 31C, 31C' as cell and culture medium input port during loading and the other fluid port 31A', 31B', 31C' of each first fluid port pair 31A, 31A', 31B, 31B', 31C, 31C' as culture medium output port during operation. Correspondingly, it is preferred to use one common second fluid port 33A of the multiple common second fluid ports 33A, 33B, 33C as cell and culture medium output port during loading and another common second fluid port 33C as culture medium and reagents, chemicals or agents input port during operation. Such an approach reduces the risk of contaminating the various fluid ports and in particular reduces the risk of contaminating culture medium and reagents, chemicals or agents used during operation with culture medium and cells added during loading.

A second operation mode involves using a single cell strain or cell strain library. In such a case, the cell strain or cells of strain library are loaded through at least one, preferably one, common second fluid port 33A using a respective first fluid port 31A', 31B', 31C' (or 31A, 31B, 31C) as output port for excess cells and culture medium and the common third fluid port 51 as output port for culture medium. During operation different culture medium and/or different reagents, chemicals or agents can be input at the other respective first fluid port 31A, 31B, 31C (or 31A', 31B', 31C'). At least one of the common second fluid ports 33B, 33C and the common third fluid port 51 are then used as output ports for the different culture medium and/or different reagents, chemicals or agents.

In a particular embodiment, the respective second end 34A, 34B, 34C of each flow input channel 30A, 30B, 30C of the multiple flow input channels 30A, 30B, 30C is in fluid connection with the common second fluid port(s) 33A, 33B, 33C through a respective interconnecting channel 36A, 36B, 36C. In an 30 embodiment, each respective interconnecting channel 36A, 36B, 36C has a substantially same channel length.

Thus, in an embodiment, the channel distance from each respective second end 34A, 34B, 34C of the flow input channels 30A, 30B, 30C to the common second fluid port 33 (see FIG. 6) or ports 33A, 33B, 33C (see FIG. 10) is preferably the same for each set 2A, 2B, 2C of cell channels. This means that the interconnecting channels 36A, 36B, 36C are used to compensate for the differences in physical distances on the substrate 10 between the respective fluid input channels 30A, 30B, 30C and the common second fluid port(s) 33A, 33B, 33C as shown in FIG. 10. Such a same distance keeps the pressure on the flow the same for each set 2A, 2B, 2C of cell channels.

Figure 12:
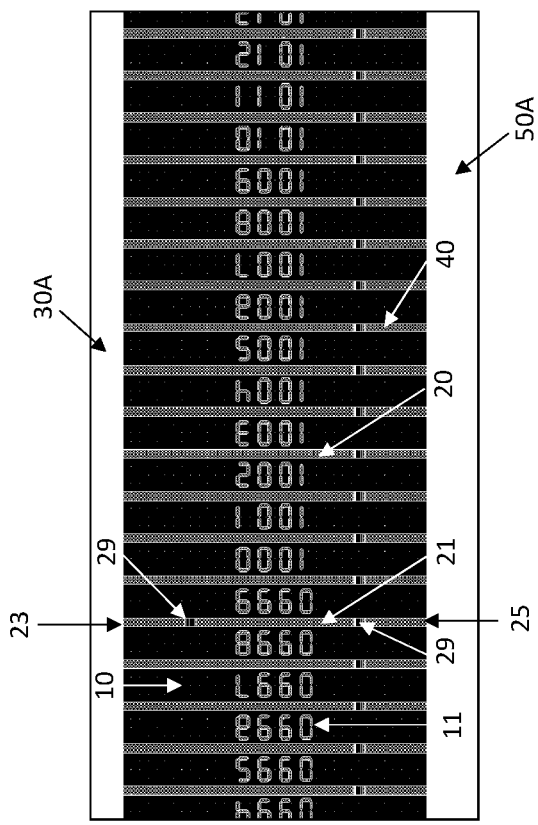
FIG. 12 schematically illustrates a magnification of the portion in box B of the microfluidic device shown in FIG. 11.
Figure 11:
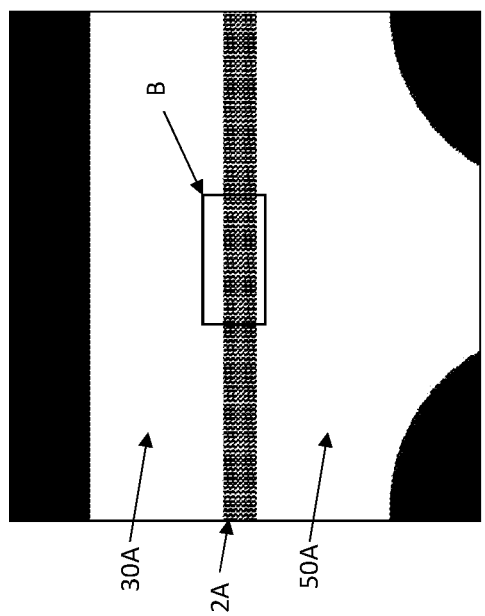
FIG. 11 schematically illustrates a magnification of the portion in box A of the microfluidic device shown in FIG. 10.

FIG. 11 schematically illustrates a magnification of the portion of the microfluidic device shown in FIG. 10 present in the box A. Correspondingly, FIG. 12 schematically illustrates a magnification of the portion of the microfluidic device shown in FIG. 11 present in the box B. This FIG. 12 illustrates two optional but preferred features of the microfluidic device.

Firstly, each cell channel 20 preferably has a respective channel identifier 11. FIG. 12 illustrates the channel identifiers 11 as respective channel numbers for the various cell channels 20. For instance, the cell channels 20 could be numbered from 0000 (or 0001) up to 9999 for a microfluidic device 1 with 10,000 (or 9,999) cell channels 20. Other identification symbols than numbers could be used as channel identifiers 11.

Figure 9:
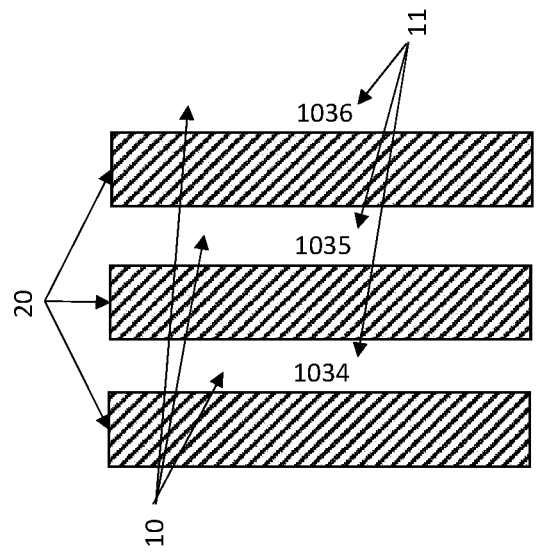
FIG. 9 schematically illustrates a magnification of cell channels with channel identifiers in a microfluidic device.

Thus, in an embodiment, see FIGS. 9 and 12, the substrate 10 of the microfluidic device comprises a respective channel identifier 11 for each spatially defined and separated cell channel 20 of the plurality of spatially defined and separated cell channels 20. The respective channel identifiers 11 are visual by imaging.

It is not absolutely necessary that every cell channel 20 has a respective channel identifier 11. Thus, in an embodiment, the substrate 10 comprises a respective channel identifier 11 for at least every Nth spatially defined and separated cell channel 20 of the plurality of spatially defined and separated cell channels 20. The parameter N can have any integer value equal to or larger than 1, , such as 1, 2, 5, 10, 20, 25, 30, 40, 50, 60, 70, 80, 90 or 100 as non-limiting but illustrative examples.

Thus, the channel identifiers 11 are preferably visually readable using, for instance, a microscope or an imaging device taking pictures or recording a video of cells present in the cell channels 20 of the microfluidic device 1. This means that cells present in a given cell channel 20 can be identified through the channel identifier 11.

Figure 8:
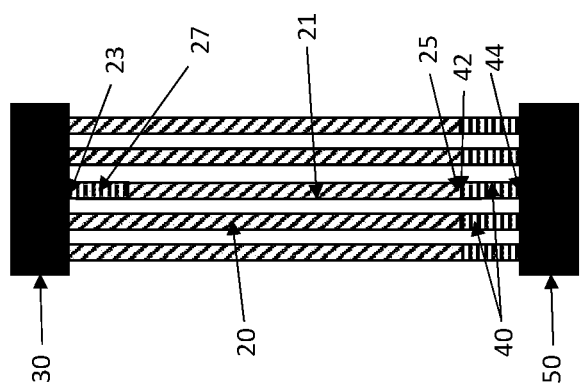
FIG. 8 schematically illustrates a magnification of cell and reference channels in a microfluidic device.

Secondly, the microfluidic device preferably comprises reference channels 21, see FIGS. 8 and 12. For instance, every $n^{th}$ cell channel 20 in the substrate 10 could be replaced by a reference channel 21 for some defined integer value of n. Alternatively, the first and/or the last cell channel 20 could be in the form of a reference channel 21. A further variant is to have one or more reference channels 21 at some other selected cell channel position(s) in the substrate 10.

The reference channels 21 are designed to prevent cells from entering and growing within the reference channels 21. This could be achieved by having a dimension of the reference channels 21 that is too small for the cells to enter the reference channels 21. Alternatively, channel restrictions can be present at or in the vicinity of the ends of the reference channels 21. Such channel restrictions thereby prevent cells from entering the reference channels 21 but still allow culture medium and any chemicals, reagents or agents to enter and flow through the reference channels 21.

The reference channels 21 can be used in order to obtain background, control or reference data, such as during imaging of the microfluidic device and the cells present therein. For instance, chemicals having a particular fluorescence or absorbance property could be added to the cells in order to determine or monitor a particular characteristic of the cells. In such a case, the fluorescence or absorbance recordings obtained from the reference channels 21 can be used as background or control reference when determining the fluorescence or absorbance in the different cell channels 20. Thus, the reference channels 21 can be used for background subtraction purposes. Another example is when cells are monitored using phase contrast microscopy, in which case the characteristic phase contrast image of the reference channel can be used to account for non-cell background.

FIG. 8 illustrates an embodiment of such reference channels 21. In this embodiment, the substrate 10 has at least one reference channel 21 arranged in between and substantially parallel with two adjacent spatially defined and separate cell channels 20 of the plurality of spatially defined and separated cell channels 20. A respective first end 23 of the at least one reference channel 21 is in fluid connection with the flow input channel 30 and comprises a cell block 27 arranged to prevent the cells from entering the at least one reference channel 21 from the respective first end 23. A respective second end 25 of the at least one reference channel 21 is in fluid connection with a first end 42 of a respective first wash channel 40 having a second end 44 in fluid connection with the flow output channel 50.

In this embodiment, the reference channels 21 are substantially the same as the cell channel 20 with regard to extension and dimension but with one major difference. The reference channels 21 comprise a cell block 27 at their respective first end 23. This cell block 27 could be in the form of a channel restriction or a channel portion with smaller dimension than the rest of the reference channels 21. The channel restriction or smaller dimension portion is selected to be too small or narrow for cells that otherwise can enter the cell channels 20. Hence, these cells cannot enter the reference channels 21 from the first end 23. The second end 25 of the reference channels 21 is connected, as the cell channels 20, to a respective first wash channel 40. This means that cells cannot enter the reference channels 21 from the second end 25 due to the selected dimension or size of the first wash channels 40.

FIG. 12 illustrates another embodiment of reference channels 21. In this embodiment, the substrate 10 has at least one reference channel 21 arranged in between and substantially parallel with two adjacent spatially defined and separated cell channels 20 of the plurality of spatially defined and separated cell channels 20. A respective first end 23 of the at least one reference channel 21 is in fluid connection with the flow input channel 30A and comprises a channel restriction 29 arranged to prevent the cells from entering the at least one reference channel 21 from the respective first end 23. A respective second end 25 of the at least one reference channel 21 is in fluid connection with the flow output channel 50A and comprises a channel restriction 29 arranged to prevent the cells from entering the at least one reference channel 21 from the respective second end 25.

In this embodiment, each reference channel 21 thereby comprises two channel restrictions 29 one at or in the vicinity of each end 23, 25 of the reference channel 21. The dimensions of the remaining part of the reference channel 21 could thereby be substantially the same as the dimensions of the cell channels 20.

In the above described embodiments, the reference channels 21 are described as being arranged in between two adjacent cell channels 20. In other embodiments, a reference channel 21 may be present at either end of a set 2A of cell channels 20 so that it lacks a cell channel 20 along one of its two longitudinal sides. It is also possible to have two reference channels 21 arranged adjacent each other.

However, it is generally preferred to have the reference channels 21 evenly distributed over the set 2A of cell channels, such as by having a reference channel 21 at every $n^{th}$ channel position in the substrate 10.

Figure 13:
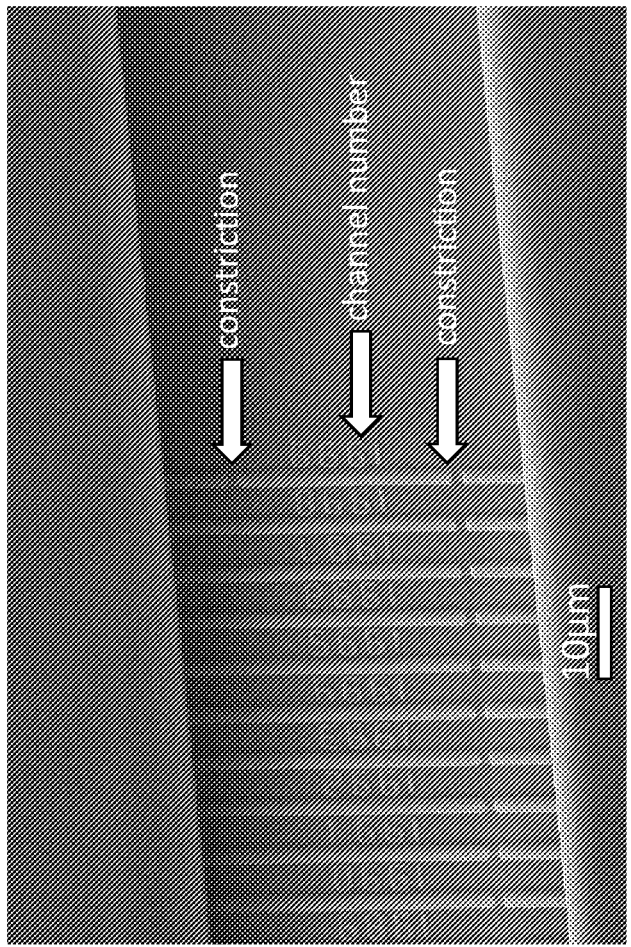
FIG. 13 is a scanning electron microscope (SEM) image of a mold for casting a microfluidic device according to an embodiment.

FIG. 13 is a SEM image of a mold that can be used for casting a microfluidic device of the embodiments. The figure shows the channel identifiers as channel numbers and shows channel restrictions used to define reference channels and the interface between a cell channel and the corresponding first wash channel.

Figure 14:
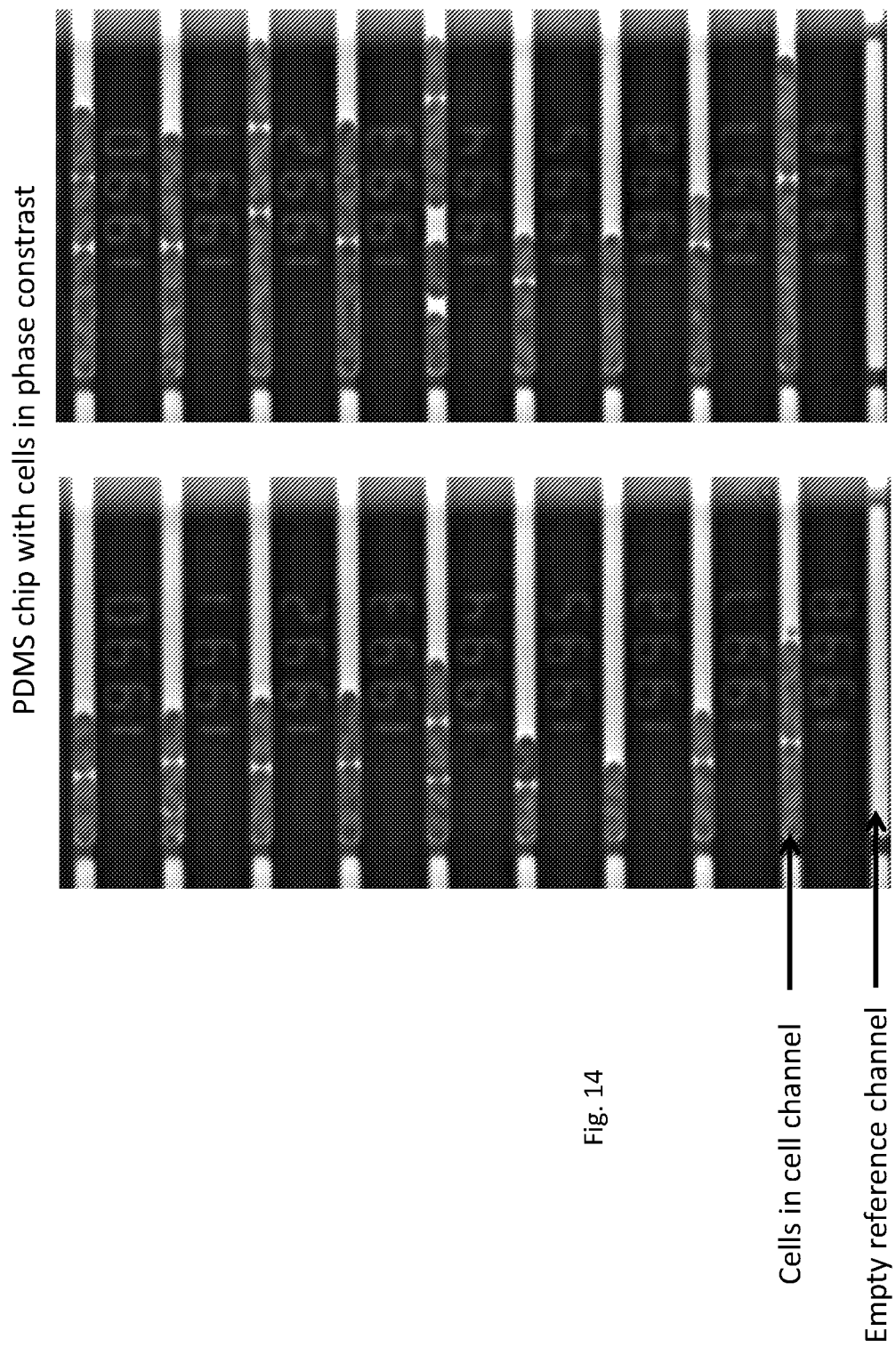
FIG. 14 illustrate phase contrast images of *Escherichia coli* cells growing in a microfluidic device according to an embodiment.

FIG. 14 illustrates phase contrast images of *Escherichia coli* cells growing in a microfluidic device according to the embodiments taken at two different points in time. The smaller dimension of the first wash channels, such as in the form of channel restrictions at the interface between first wash channels and cell channels, efficiently prevents the *E. coli* cells from growing out to the left in the figure, i.e. enter the first wash channels. The channel at the bottom of the figure is an empty reference channel. The double restrictions at either end of the reference channel prevent any *E. coli* cells from entering the reference channel. The channel identifiers are visible in the phase contrast images, thereby enabling identification of individual cell channels and the *E. coli* cells growing therein.

The substrate of the microfluidic device may be made of any transparent material, such as plastic material, in which the structures constituting the cell channels, the first wash channels, the first fluid port, the second fluid port, the flow input channel, the flow output channel and the third fluid port can be defined. Non-limiting examples of suitable materials include ZEONEX® and ZEONOR®, which are cyclic olefin polymers (COP) marketed by ZEON Chemicals L.P. and TOPAS®, which are cyclic olefin copolymers (COC) marketed by Topas Advanced Polymers. These materials have excellent optical characteristics in terms of transmission and background fluorescence. They also have good flow characteristics when heated and may therefore replicate small structures allowing formation of substrates of the microfluidic device.

Other examples of suitable materials for the substrate include glasses, polydimethylsiloxane (PDMS), poly (methyl methacrylate) (PMMA), polycarbonate (PC), polypropylene (PP), polytetrafluoroethylene (PTFE), polyethylene terephthalate (PET) and poly(p-phenylene sulfide) (PPS).

The cover plate illustrated in FIGS. 2 and 4 may be manufactured in various materials that are preferably transparent to allow imaging. Non-limiting examples include glass and plastic materials.

In operation the microfluidic device is preferably connected to a fluidic manifold to form a culturing system comprising the microfluidic device and the fluidic manifold. The fluidic manifold is configured to distribute culture medium and any reagents, chemicals or agents to the cell channels using at least one computer-controlled pump. The fluidic manifold is preferably configured to enable change of culture media, distribution of reagents, chemicals or agents using the computer-controlled and preprogramed pumps. In a particular embodiment, the reagents, chemicals or agents and cell culture media can be maintained at different temperatures throughout the experiment.

Figure 16:
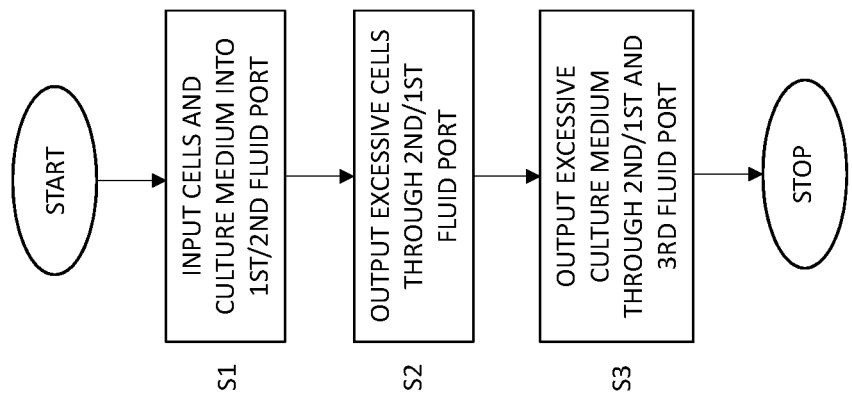
FIG. 16 is a flow chart illustrating a method of loading a microfluidic device according to an embodiment.

FIG. 16 is a flow chart illustrating a method of loading a microfluidic device according to an embodiment. The method comprises inputting cells and culture medium in one of a first fluid port and a second fluid port of the microfluidic device in step S1 to allow the cells and culture medium to flow through a flow input channel of the microfluidic device and into a plurality of spatially defined and separated cell channels. A respective first end of the plurality of spatially defined and separated cell channels is in fluid connection with the flow input channel having a first end in fluid connection with the first fluid port and a second end in fluid connection with the second fluid port. A next step S2 comprises outputting excessive cells through the other of the first fluid port and the second fluid port and step S3 comprises outputting culture medium through the other of the first fluid port and the second fluid port and through a third port in fluid connection with a flow output channel. A respective second end of the plurality of spatially defined and separated cell channels is in fluid connection with a first end of a respective first wash channel having a second end in fluid connection with the flow output channel. The first wash channels have a dimension too small to accommodate the cells.

Steps S2 and S3 generally take place at the same time as the input cells and culture medium enter the microfluidic device and its various channels.

The microfluidic device of the embodiments can be used for various applications. An example of such application is antibiotic susceptibility testing (AST). For example, the microfluidic device 1 shown in FIG. 10 can be used for this purpose. In such a case, the sample strain can be loaded from, for instance, the common second fluid port 33A using the first fluid ports 31A', 31B', 31C' as output ports for excess cells and culture medium and the common third fluid port 51 as output port for culture medium and for sucking cells into the cell channels. In an example, during loading culture medium is flown from the common second fluid port 33C to the common second fluid port 33B to prevent contaminating the common second fluid port 33C. After cell loading culture medium preferably flows from the common second fluid port 33C using the first fluid ports 31A', 31B', 31C' and the common third fluid port 51 as output ports. At this stage growth of the cells in the cell channels can be monitored for some time, 0 min to days, while imaging the cells in the different cell channels. The AST test starts by flowing different antibiotics or a same antibiotic but at different concentrations into the different sets 2A, 2B, 2C of cell channels using the first fluid ports 31A, 31B, 31C as input ports, while using the common second fluid ports 33A, 33B, 33C and the common third fluid port 51 as output ports. Susceptibility is monitored by the phenotypic response to antibiotic in the different cell channels. For example, it is possible to determine the average growth rate and the cell to cell distribution of growth rates just by monitoring the length extension in phase contrast using automatics images analysis routines. These measurements can be averaged over cells in many cell channels such that it is possible to determine minute phenotypic changes within a few minutes. Phenotypic changes can also be in morphological changes, such as the compaction of DNA or changes in membrane structure or in integrity. Some phenotypic changes are best studied by addition of test agents, such as 4',6-diamidino-2-phenylindole (DAPI) and SYTOX® fluorescent stains, that can be monitored in a florescence channel.

The phenotypic AST can be followed by an in situ genotyping test where the presence, absence or abundance of significant genes, DNA sequences or RNA species are determined by for example fluorescence in situ hybridization (FISH), in situ sequencing or isothermal amplification using for example loop mediated isothermal amplification (LAMP) or hybridization and ligation of one or more specific padlock probes followed by rolling circle amplification (RCA).

FIG. 15 are phase contrast images taken of a microfluidic device during an AST test in which chloramphenicol-susceptible (minimum inhibitory concentration (MIC)≈4 µg/ml) and chloramphenicol-resistant (MIC>12 µg/ml) *E. coli* strains were loaded at different cell channels in a microfluidic device corresponding to FIG. 10. After cell loading both strains were exposed to 6 µg/ml chloramphenicol. The images that are taken 15 min apart clearly show that the chloramphenicol-susceptible strain has grown much less than the chloramphenicol-resistant strain.

Figure 17:
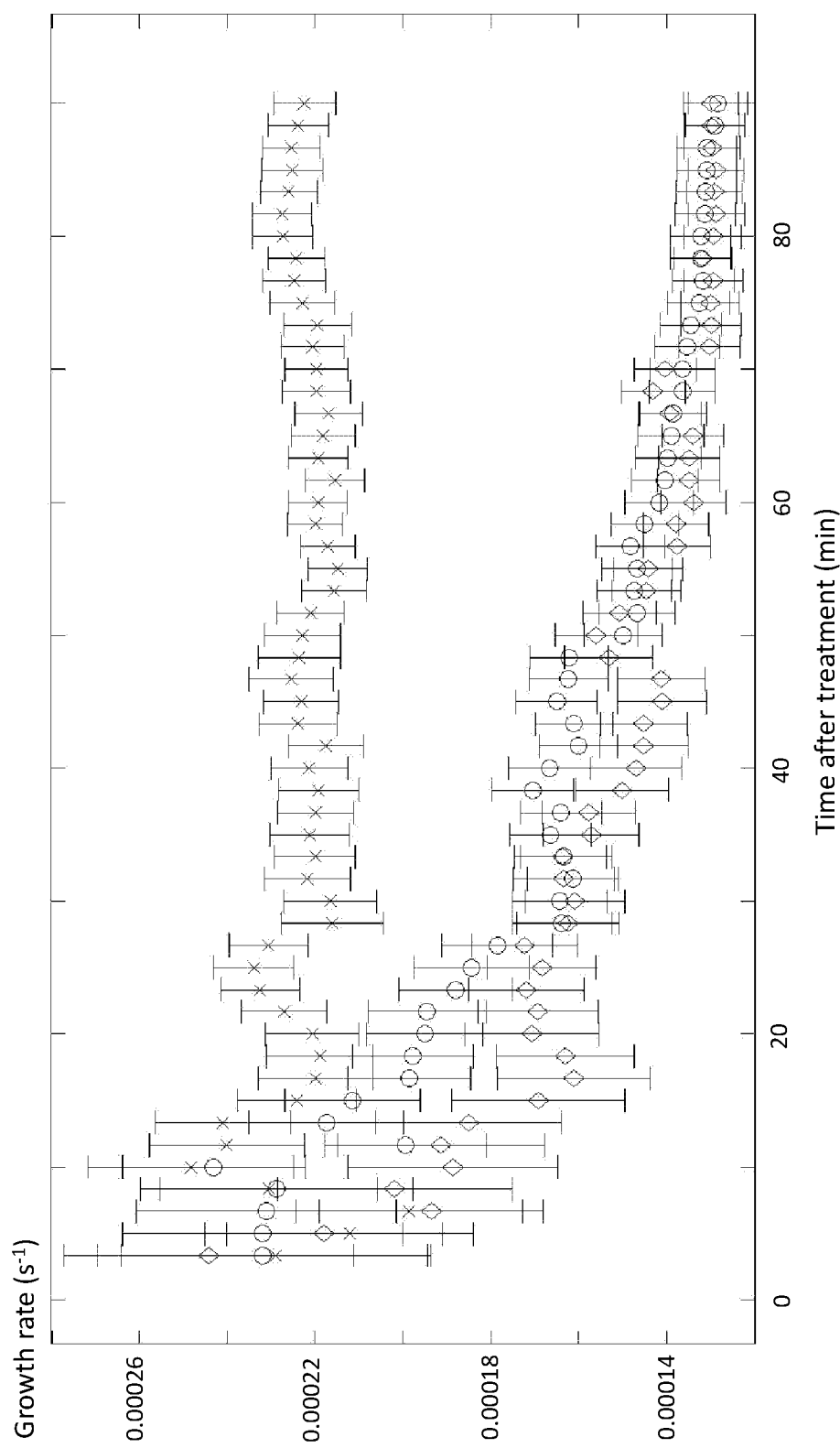
FIG. 17 shows the average growth rate response of one erythromycin-resistant and two erythromycin-susceptible *E. coli* strains when exposed to 120 µg/ml erythromycin at time=0 min.

FIG. 17 displays average growth rates for three different *E. coli* strains when exposed to erythromycin at 120 µg/ml at time 0 min, when the three strains are loaded into respectively set 2A, 2B, 2C of cell channels 20 in a microfluidic device 1 corresponding to FIG. 10. The resistant strain indicated by "x" has a MIC of 256 µg/ml, whereas the non-resistant strains indicated by circles and diamonds have MIC~12 µg/ml. The figure clearly shows that the resistant strain can be distinguished from the susceptible stains in less than 20 min.

Figure 18:
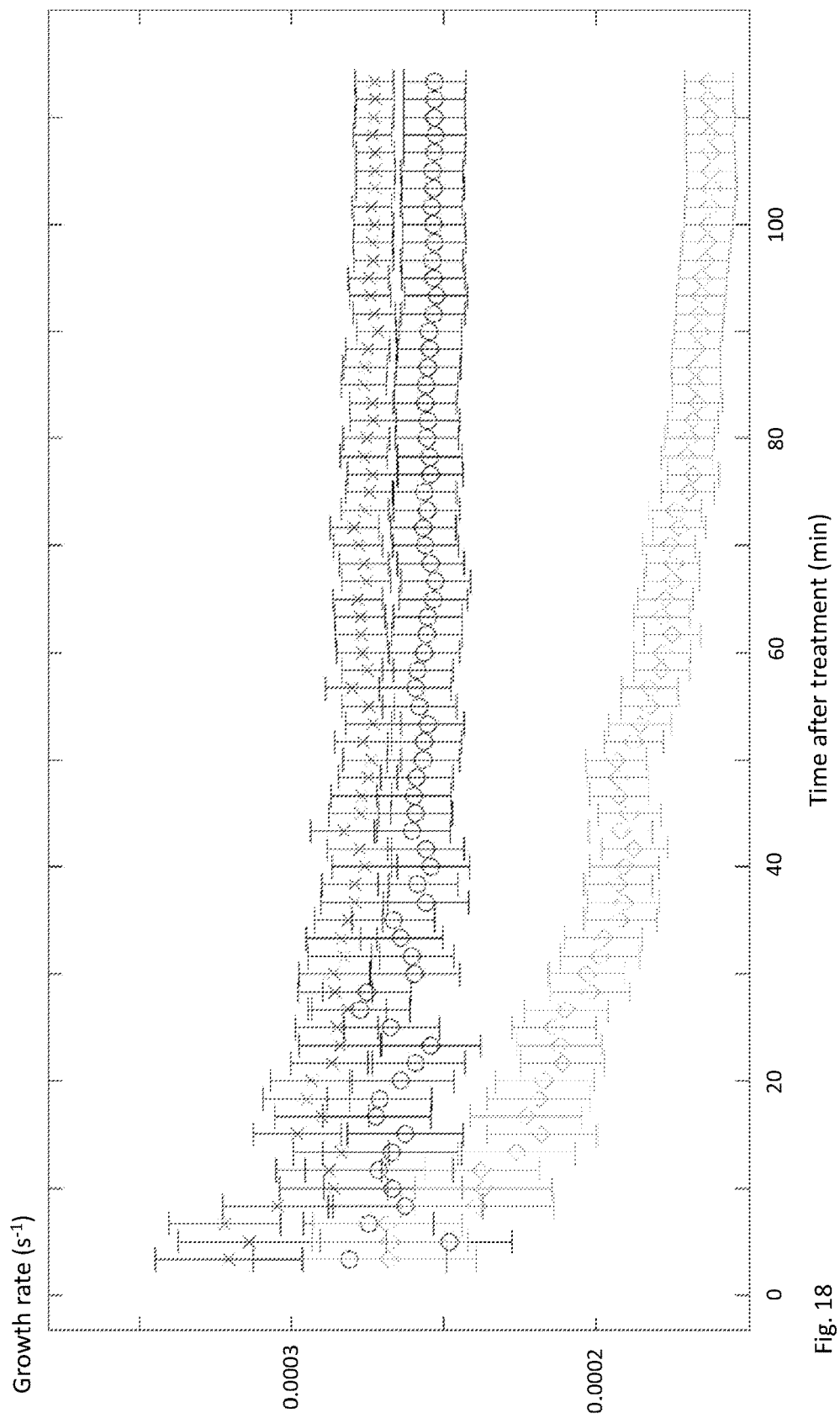
FIG. 18 shows the average growth rate response for a ciprofloxacin resistant *E. coli* strain when exposed to (1) no drug (marked "x"), (2) erythromycin (120 µg/ml, marked with diamonds) or (3) ciprofloxacin (10 µg/ml, marked with circles) at time=0 min.

FIG. 18 displays average growth rate response, as determined by phase contrast time lapse imaging, for an *E. coli* strain that is resistant to ciprofloxacin (DA20859 Eco gyrA1-S83L gyrA2-D87N parC-S801 MIC~30 µg/ml) loaded into respective sets 2A, 2B, 2C of cell channels 20 in a microfluidic device 1 corresponding to FIG. 1. The *E. coli* strain was exposed to (1) no drug marked with "x", (2) erythromycin at 120 µg/ml marked with diamonds or (3) ciprofloxacin 10 µg/ml marked with circles. The time point 0 min corresponds to the start of the treatment. The curve corresponding to treatment with the drug (erythromycin) for which the strain is susceptible can be distinguished from the no treatment curve in <10 min. The curve corresponding to treatment with the drug for which the strain is susceptible can be distinguished from the curve corresponding to the drug (ciprofloxacin) for which the strain is resistant in <15 min.

Thus, an embodiment relates to a method for antibiotic susceptibility testing. The method comprises loading bacteria cells into a plurality of spatially defined and separated cell channels of a microfluidic device according to the embodiments. The method also comprises exposing bacteria cells in different spatially defined and separated cell channels of the plurality of spatially defined and separated cell channels to different antibiotics and/or to different concentration of an antibiotic. The method further comprises determining antibiotic susceptibility of the bacteria cells based on a respective phenotype characteristic of the bacteria cells in the plurality of spatially defined and separated cell channels.

Thus, a respective phenotype characteristic is monitored and determined for the bacteria cells and where this phenotype characteristic is representative of the antibiotic susceptibility of the bacteria cells. In a preferred embodiment, the phenotype characteristic is preferably at least one of a respective growth rate, a respective degree of nucleoid compaction, a respective degree of metabolic activity and a respective degree of membrane integrity of the bacteria cells in the plurality of spatially defined and separated cell channels.

The microfluidic device of the embodiments can be used for culturing and monitoring various types of cells including, but not limited to, bacterial cells, archaeal cells, eukaryotic cells, such as yeast cells, mammalian cells, human cells, etc.

The microfluidic device of the embodiments can be used for characterizing cells, such as a library of cell strains. The characterization can be in the form of determining at least one phenotypic characteristic of the cell strains and/or in situ genotyping genetic material of the cell strains. An example of phenotypic characterization and in situ genotyping of a library of cell strains is disclosed in the co-pending patent application no. PCT/SE2015/050227. . In particular, the microfluidic device then allows monitored phenotypic characteristics and in situ determined genotypes to be connected in a highly parallel way. This means that a vast library of cell strains with different genotypes can be processed in parallel in the microfluidic device in order to connect the monitored phenotypic characteristics to the different genotypes of the cell strains.

The library of cell strains can be obtained according to various techniques within genome engineering. For instance, Multiplex Automated Genomic Engineering (MAGE) can be used to create several billions of different mutant genomes per day (Wang et al. *Nature*, 2009, 460: 894-898). Other techniques that can be used to create a library of cells include Clustered Regularly Interspaced Short Palindromic Repeats (CRISPR) associated protein 9 (Cas9) (Wang et al., *Science*, 2014, 343: 80-84; Koike-Yusa et al., *Nature Biotechnology*, 2014, 32: 309-312; Zhou et al., *Nature*, 2014, 509: 487-491) or large-scale RNA interference (Berns et al., *Nature*, 2004, 428: 431-437).

The microfluidic device then allows cells of each cell strain in the library to be kept and cultured separately from cells of other cell strains and or other genotypes. Hence, each cell strain has a respectively spatially defined and separated cell channel in the microfluidic device in which the cells can grow and be studied.

The cells cultured at the spatially defined and separated cell channels in the microfluidic device can preferably be exposed to various physical and/or chemical stimuli or agents without being washed away, in order to monitor the response of the cells to the physical and/or chemical stimuli or agents. For instance, various chemical test agents, such as nutrients, drugs, antibiotics, gene expression inducers or repressors, could be added to the culture medium and thereby contact the cells. The phenotypic characteristics of the cell strains in terms of the response of the cells of the different cell strains to the various test agents can then be determined, for instance, using microscopy. Correspondingly, the temperature, pH, pressure, flow, gases, light exposure or mechanical stress that the cells are exposed to could be changed and the response of the cells of the different cell strains to such changing physical conditions can be determined, for instance, using microscopy.

The cells strains have different genotypes as represented by having different variable regions in at least one part of their genetic material. The variable region is typically present in the genome of the cell strains. Alternatively, the variable region is present in a mobile genetic element, such as plasmid or vector, and hence does not necessarily have to be stably incorporated into the genome of the cells. In the following, the embodiments are mainly discussed with regard to the variable region being present in the genome. However, alternative embodiments are possible where the variable region and the further DNA elements mentioned herein are instead present in a plasmid or other mobile genetic element of the cell strains. The variable region, or parts thereof, can also be present in unstable genetic elements, such as transposons, viruses or phages. Such encoding will sometimes have advantages in terms of amplifying the variable sequence before fixing the cells for in situ sequencing, for example by specifically excising or circularizing parts of the variable region from the dsDNA genome before fixing the cells.

In an embodiment, the method also comprises randomly seeding cells of the cell strains at the spatially defined and separated cell channels in the microfluidic device. The randomly seeding of cells is preferably performed so that each cell channel only comprises cells of a same genotype, i.e. of the same cell strain.

An advantage of the embodiments is that the genetic identity, i.e. genotype, of the cells does not need to be determined and known prior to seeding of the cells in the microfluidic device. Thus, there is no need to keep the cells in the cell library sorted prior to seeding in terms of having to know the genetic identity of each cell strain and continuously monitoring the position of each genotype throughout the method. This means that the present embodiment in clear contrast first analyzes the phenotypic characteristics in parallel without any knowledge of the genotype and then determines the genotypes and connects them to the phenotypic characteristics.

The phenotypic characteristic determined for each cell strain in the library is preferably a phenotypic characteristic corresponding to each genotype in the library. Thus, the cells in the library are genetically different cells having different genotype, i.e. a respective genotype per cell strain. The differences in genotype imply that the cells will have different phenotypic characteristics corresponding to each respective genotype.

In an embodiment, the phenotypic characteristics of the cells are determined using microscopy. Microscopy for monitoring and determining phenotypes has several advantages as compared to prior art technologies. For instance, fluorescence microscopy allows for extensive time laps of cell linages over many generations, single molecule detection sensitivity and the possibility to monitor temporal responses to changing growth conditions in any way.

Non-limiting but illustrative examples of phenotypic characteristics that can be monitored and determined according to the embodiments using microscopy include cell morphology, spatial and/or temporal expression patterns of various molecules, such as ribonucleic acid (RNA) or proteins, levels of specific metabolites, lifespan or growth rate changes, such as in response to addition of different physical or chemical stimuli or agents, cell-to-cell variations in gene expression levels, embryo development, brightness of reporter proteins or RNA aptamers, etc.

The phenotypic characterization of the cell strains can, thus, be performed in parallel under a microscope for a long period of time if needed. The phenotypic characterization is furthermore performed without knowledge of the genotype of the various cell strains in the library. In clear contrast, the phenotypic characterization instead determines respective phenotypic characteristics for each spatially defined and separated cell channel in the microfluidic device. For instance, assume that the relevant phenotypic characteristic to be determined for the cell strains is gene expression of a target gene for a fluorescence reporter protein, with a variable gene regulatory region or coding sequence, following addition of a test agent. In such a case, the microscope can be used to take an image over the microfluidic device in which the respective gene expression levels can be visually determined. Each individual gene expression level can then be quantized to get a respective value for each cell channel in the microfluidic device. Thus, the output of the determination of the phenotypic characterization could be a list or matrix of one or more respective values for each cell channel in the microfluidic device. If each cell channel is assigned a respective channel identifier as previously described herein, the phenotypic characteristic measured for cells in a cell channel can then be associated with the channel identifier assigned to that cell channel.

In an embodiment, determining the phenotypic characteristic comprises determining the phenotypic characteristic of each cell strain during culturing of the cells in the microfluidic device using microscopy. Examples of microscopy technologies that can be used in the embodiments include, for instance, bright field microscopy, phase contrast microscopy, fluorescence microscopy, light sheet microscopy, or any type of super resolution imaging modality such as stimulated emission depletion (STED) microscopy, photoactivated localization microscopy (PALM), near-field scanning optical microscopy (NSOM), 4Pi microscopy, structured illumination microscopy (SIM), ground state depletion (GSD) microscopy, spectral precision distance microscopy (SPDM), stochastic optical reconstruction microscopy (STORM). Furthermore, Intracellular Single Particle Tracking (SPT) or Fluorescence Correlation Spectroscopy (FCS) could also be used. Microscopy analysis can be made at fixed time points or using time lapse imaging.

Other measurements of the phenotypes are also possible, such as measuring mechanical properties using atomic force microscopy, membrane potential using indicator dyes or micro electrodes, small molecule secretion using imaging mass spectrometry or specified biosensor arrays. Near-field optical array detectors directly connected to the culturing device are also possible.

Once the phenotypic characteristics of the cell strains have been determined the cells are preferably fixated in the cell channels in the microfluidic device. Cell fixation can be performed according to techniques well known in the art. For instance, formaldehyde, methanol, or ethanol can be used for cell fixation. In a non-limiting example cells are fixed with 4% formaldehyde for about 15 minutes or 3% (w/v) paraformaldehyde in phosphate buffered saline (PBS) for about 30 minutes.

In an embodiment, the fixated cells are permeabilized prior to in situ genotyping. Various protocols traditionally employed for cell permeabilization can be used according to the embodiments. For instance, Triton X-100 (such as 0.25% Triton X-100) or another surfactant, such as nonionic surfactant, can be used. Alternatively, ethanol, such as 70% ethanol, can be used for cell permeabilization. Further examples include hydrochloric acid, such as 0.1 M hydrochloric acid, optionally combined with a protease, such as pepsin, e.g. 0.01% pepsin, or lysozyme to degrade the bacterial cell wall.

The in situ genotyping comprises in situ genotyping at least a part of a variable region of each cell strain in the cell channels in the microfluidic device. Hence, it is not absolutely necessary to in situ genotype the complete variable region of each cell strain. Hence, in situ sequencing as used herein comprises in situ sequencing at least a part of the variable region or indeed the complete variable region. The in situ sequencing preferably outputs information showing any nucleotide differences in the variable region between different cell strains and where these nucleotide differences give rise to different phenotypes.

In an embodiment, in situ genotyping is based on the technology fluorescent in situ sequencing (FISSEQ) as described for example in *Science,* 2014, 343(6177): 1360-1363. . Briefly, in FISSEQ cDNA amplicons within the cell are generated in the fixed cells using reverse transcriptase and incorporation of aminoallyl deoxyuridine 5'-triphosphate (dUTP) during reverse transcription (RT). The cDNA is refixed using BS(PEG)9, , an amine-reactive linker with a 4 nm spacer. The cDNA fragments are then circularized before rolling circle amplification (RCA). BA(PEG)9 is then used to cross-link the RCA amplicons containing aminoallyl dUTP. SOLiD sequencing by ligation can then be used to sequence the relevant sequence in the RCA amplicons to get the nucleotide sequence of the variable region.

In an embodiment, in situ genotyping the variable region preferably comprises in situ sequencing by ligation of the variable region or at least a portion thereof in the cell channels in the microfluidic device. Sequencing by ligation relies upon the sensitivity of deoxyribonucleic acid (DNA) ligase for base pair mismatches. Generally, the variable region to be sequenced is preferably in the form of a single stranded DNA sequence, flanked on at least one end by a known sequence that will function as anchor primer-binding sequence. An anchor primer that is complementary to the known sequence is brought to bind to the known sequence.

A mixed pool of probe oligonucleotides, typically eight to nine bases long, is then brought in, labelled, typically with a fluorescent dye, according to the position that will be sequenced. These labelled oligonucleotides hybridize to the variable region, next to the anchor primer and DNA ligase preferentially joins an oligonucleotide to the anchor primer when its nucleotide sequence matches the unknown variable region. Based on the fluorescence produced by the molecule, one can infer the identity of the base at this position of the variable region.

The oligonucleotide probes may also be constructed with cleavable linkages, which can be cleaved after identifying the label. This will both remove the label and regenerate a 5'-phosphate on the end of the ligated probe, thereby enabling a new round of ligation. This cycle of ligation and cleavage can be repeated several times to read longer sequences. This technique sequences every $Q^{th}$ base in the variable region, where Q is the length of the probe left behind after cleavage. In order to sequence the skipped positions in the variable region, the anchor primer and the ligated oligonucleotides may be stripped of the variable region, and another round of sequencing by ligation is started with an anchor primer that is one or more bases shorter.

Another technique is to do repeated rounds of a single ligation where the label corresponds to different positions in the probe, followed by stripping the anchor primer and ligated probe.

Sequencing by ligation can be proceeded in either direction (5'-3' or 3'-5') depending on which end of the oligonucleotide probes that is blocked by the label.

In an embodiment, the sequence that is sequenced is preferably a cDNA sequence obtained by reverse transcription of an RNA transcript obtained from the variable region. In this embodiment, the variable region is flanked by at least one known sequence to which the anchor primer will bind.

Sequencing by ligation can be performed on fixated cells to achieve an in situ sequencing by ligation of the variable region or at least a portion thereof in the cell channels in the microfluidic device, see for instance *Science* 2014, 343: 1360-1363 and *Nature Methods* 2013, 10: 857-860, , the teachings of which are hereby incorporated by reference with regard to performing in situ sequencing by ligation.

Briefly, in one variant, RNA obtained from the variable region, or a barcode, is copied to cDNA by reverse transcription, followed by degradation of the mRNA strand using an RNase. In a first embodiment, a padlock probe binds to the cDNA with a gap between the probe ends over the bases that are targeted for sequencing by ligation. This gap is filled by DNA polymerization and DNA ligation to create a DNA circle. In a second embodiment, cDNA circulation is carried out by ssDNA ligation only. In a third embodiment, dsDNA including at least a part of the variable sequence and neighboring DNA is excised from the surrounding DNA, by for example restriction enzymes or transposases. The excised dsDNA can then be digested to ssDNA by endonucleases in order to self-hybridize and ligate to form a circular DNA.

In a variant, the variable region to be sequenced is directly amplified from dsDNA, either chromosomal or in a mobile genetic element. In this case the dsDNA can be cut with a restriction enzyme close to the variable region and the dsDNA is made single stranded by an exonuclease. This ssDNA can be amplified by a method that normally works on cDNA but without the need of expressing an RNA. This method relieves the constraints to design DNA region near the variable region. For example, the variable region can be filled in by a gapfill padlock reaction.

As an alternative to gapfill, it is possible to use a relatively long variable region (10-25 bp) and to hybridize a set of ssDNA oligonucleotides to the variable regions. The binding energies of the oligonucleotides are chosen such that only the specific oligonucleotide binds at the choose hybridization and ligation temperature. Say for example that the library contains 4000 variants encoded in a 15 bp variable region which would allow for $4^{15} \sim 10^9$ variants, it is possible to pick the 4000 variant such that there are no cross hybridizing probes. After hybridization of the oligonucleotide and the padlock probe, the probe is ligated into a circle that can be amplified.

In either case, the formed DNA circle is amplified by target-primed rolling circle amplification (RCA) generating a rolling circle product (RCP) that is subjected to sequencing by ligation. An anchor primer is hybridized next to the targeted sequence before the ligation of oligonucleotides probes. In an embodiment, the oligonucleotide probes consist of four libraries of 9-mers, with eight random positions (N) and one fixed position (A, C, G or T). Each library is labeled with one of four fluorescent dyes. The oligonucleotide probe with best match at the fixed position will be incorporated by ligation along with its fluorescent label. The sample is imaged and each RCP displays the color corresponding to the matched base. The oligonucleotide probe is washed away before the application of oligonucleotide probes for the next base. The steps of ligation, washing, imaging and stripping are iterated until the desired number of bases has been read.

In another embodiment, in situ genotyping comprises in situ sequencing by synthesis of the variable region or at least a portion thereof in the cell channels in the microfluidic device.

For instance, four types of modified dNTPs containing a terminator that blocks further polymerization are added. The terminator also contains a fluorescent label that can be detected by camera. Non-incorporated nucleotides are washed away and images of the fluorescently labeled nucleotides are taken. The fluorescent label along with the terminator are chemically removed from the DNA allowing for the next cycle of sequencing to being.

The result of the in situ genotyping is preferably the nucleotide sequence of the variable region or at least a portion thereof for each cell strain. Each nucleotide sequence is furthermore connected to a respective cell channel in the microfluidic device, such as by using the channel identifiers. This is possible since the genotyping is performed as an in situ genotyping, such as in situ sequencing by ligation or synthesis. In situ here implies that the genotyping is performed on site or in position, i.e. in the cell channels in the microfluidic device.

The output of the previously described phenotyping was a respective determined phenotypic characteristic for each cell channel in the microfluidic device, such as in the form of a list or matrix listing the phenotypic characteristic(s) determined for each cell channel as identified by the channel identifiers. The output of the in situ genotyping is the nucleotide sequence determined for the variable regions at each cell channel in the microfluidic device. This output may also be in the form of a list or matrix listing the nucleotide sequence determined for each cell channel as identified by the channel identifiers.

Each respective phenotypic characteristic can then be connected or associated with each respective genotype based on the cell channels in the microfluidic device. For instance, the phenotypic characteristic determined for the cells of the cell strain at cell channel no. P is a result of the genotype of the cells of this cell strain and this genotype is obtained from the nucleotide sequence determined for cell channel no. P. Hence, the connection of phenotype and genotype can be achieved simply by matching the phenotypic characteristics and genotypes determined for each cell channel in the microfluidic device.

In the above described application, the microfluidic device of the embodiments is used for combined phenotype and in situ genotype determination of a library of cell strains. The microfluidic device may alternatively be used for merely phenotype determination or merely in situ genotype determination.

Hence, it is not necessary to perform both phenotype and in situ genotype determination of cells loaded into the microfluidic device.

An aspect of the embodiments therefore relates to a method for in situ genotyping cells. The method comprises loading cells into a plurality of spatially defined and separated cell channels of a microfluidic device according to the embodiments. The method also comprises fixating the cells in the plurality of spatially defined and separated cell channels. The method further comprises in situ genotyping the cells in the plurality of spatially defined and separated cell channels.

Another aspect of the embodiments relates to a method for phenotype characterization of cells. The method comprises loading cells into a plurality of spatially defined and separated cell channels of a microfluidic device according to the embodiments. The method also comprises growing or culturing the cells in the plurality of spatially defined and separated cell channels. The method further comprises real-time monitoring a phenotype characteristic of the cells in the plurality of spatially defined and separated cell channels.

A further aspect of the embodiments relates to a method of characterizing a library of a plurality of cell strains having different variable regions in at least one part of the genetic material of the cell strains. The method comprises loading cells of the cell strains of the library into a plurality of spatially defined and separated cell channels of a microfluidic device according to the embodiments. The method also comprises growing or culturing the cells of the cell strains in the plurality of spatially defined and separated cell channels. The method further comprises determining a phenotypic characteristic of each cell strain in the microfluidic device, preferably by real-time monitoring a respective phenotype characteristic of the cells of the cell strains in the plurality of spatially defined and separated cell channels. The method additionally comprises fixating the cells of the cell strains in the spatially defined and separated cell channels in the microfluidic device. The method further comprises in situ genotyping the variable region of each cell strain in the spatially defined and separated cell channels in the microfluidic device. Finally, the method comprises connecting each respective phenotypic characteristic to each respective genotype based on the spatially defined and separated cell channels in the microfluidic device, preferably based on the respective channel identifiers or the respective positions of the spatially defined and separated cell channels in the substrate of the microfluidic device.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A microfluidic device comprising:
    a substrate having a plurality of spatially defined and separated cell channels having a dimension to accommodate cells;
    a respective first end of said plurality of spatially defined and separated cell channels is in fluid connection with a flow input channel having a first end in fluid connection with a first fluid port and a second end in fluid connection with a second fluid port;
    a respective second end of said plurality of spatially defined and separated cell channels is in fluid connection with a first end of a respective first wash channel having a second end in fluid connection with a flow output channel, wherein said flow output channel is in fluid connection with a third fluid port; and
    said first wash channels have a dimension too small to accommodate said cells.

2. The microfluidic device according to claim 1, wherein said flow input channel has a dimension sufficient large to allow said cells to flow through said flow input channel.

3. The microfluidic device according to claim 1, wherein each spatially defined and separated cell channel of said plurality of spatially defined and separated cell channels is flanked along at least one of its longitudinal sides with a respective second wash channel having a first end in fluid connection with said flow input channel and a second end in fluid connection with said flow output channel, wherein said second wash channels have a dimension too small to accommodate said cells.

4. The microfluidic device according to claim 1, wherein said substrate has at least one reference channel arranged in between and substantially parallel with two adjacent spatially defined and separated cell channels of said plurality of spatially defined and separated cell channels;
    a respective first end of said at least one reference channel is in fluid connection with said flow input channel and comprises a cell block arranged to prevent said cells from entering said at least one reference channel from said respective first end; and
    a respective second end of said at least one reference channel is in fluid connection with a first end of a respective first wash channel having a second end in fluid connection with said flow output channel.

5. The microfluidic device according to claim 1, wherein said substrate has at least one reference channel arranged in between and substantially parallel with two adjacent spatially defined and separated cell channels of said plurality of spatially defined and separated cell channels;

a respective first end of said at least one reference channel is in fluid connection with said flow input channel and comprises a channel constriction arranged to prevent said cells from entering said at least one reference channel from said respective first end; and a respective second end of said at least one reference channel is in fluid connection with said flow output channel and comprises a channel constriction arranged to prevent said cells from entering said at least one reference channel from said respective second end.

6. The microfluidic device according to claim 1, wherein said substrate comprises a respective channel identifier for at least every Nth spatially defined and separated cell channel of said plurality of spatially defined and separated cell channels; and said respective channel identifiers being visual by imaging.

7. The microfluidic device according to claim 1, wherein said substrate has multiple sets of said plurality of spatially defined and separated cell channels, multiple flow input channels and multiple flow output channels;

said respective first end of said plurality of spatially defined and separated cell channels in each set of said multiple sets is in fluid connection with a respective flow input channel of said multiple flow input channels;

said respective second end of said first wash channels in each set of said multiple sets is in fluid connection with a respective flow output channel of said multiple flow output channels;

a respective first end of each flow input channel of said multiple flow input channels is in fluid connection with a respective first fluid port;

a respective second end of each flow input channel of said multiple flow input channels is in fluid connection with a common second fluid port; and each flow output channel of said multiple flow output channels is in fluid connection with a common third fluid port.

8. The microfluidic device according to claim 7, wherein said respective first end of each flow input channel of said multiple flow input channels is in fluid connection with multiple respective first fluid ports;

said respective second end of each flow input channel of said multiple flow input channels is in fluid connection with multiple common second fluid ports.

9. The microfluidic device according to claim 7, wherein said respective second end of each flow input channel of said multiple flow channels is in fluid connection with said common second fluid port through a respective interconnecting channel, wherein each respective interconnecting channel has a substantially same channel length.

10. A method of loading a microfluidic device according to claim 1, said method comprising:

inputting cells and culture medium in one of a first fluid port and a second fluid port of said microfluidic device to allow said cells and culture medium to flow through a flow input channel of said microfluidic device and into a plurality of spatially defined and separated cell channels, wherein a respective first end of said plurality of spatially defined and separated cell channels is in fluid connection with said flow input channel having a first end in fluid connection with said first fluid port and a second end in fluid connection with said second fluid port;

outputting excessive cells through the other of said first fluid port and said second fluid port; and outputting culture medium through the other of said first fluid port and said second fluid port and through a third port in fluid connection with a flow output channel, wherein a respective second end of said plurality of spatially defined and separated cell channels is in fluid connection with a first end of a respective first wash channel having a second end in fluid connection with said flow output channel, said first wash channels have a dimension too small to accommodate said cells.

11. A method for antibiotic susceptibility testing, said method comprising:

loading bacteria cells into a plurality of spatially defined and separated cell channels of a microfluidic device according to claim 1;

exposing bacteria cells in different spatially defined and separated cell channels of said plurality of spatially defined and separated cell channels to different antibiotics and/or to different concentrations of an antibiotic; and determining antibiotic susceptibility of said bacteria cells based on a respective phenotype characteristic, preferably at least one of a respective growth rate, a respective degree of nucleoid compaction, a respective degree of metabolic activity and a respective degree of membrane integrity, of said bacteria cells in said plurality of spatially defined and separated cell channels.

12. A method for in situ genotyping cells, said method comprising:

loading cells into a plurality of spatially defined and separated cell channels of a microfluidic device according to claim 1;

fixating said cells in said plurality of spatially defined and separated cell channels; and in situ genotyping said cells in said plurality of said spatially defined and separated cell channels.

13. A method for phenotype characterization of cells, said method comprising:

loading cells into a plurality of spatially defined and separated cell channels of a microfluidic device according to claim 1;

growing said cells in said plurality of spatially defined and separated cell channels; and real-time monitoring a phenotype characteristic of said cells in said plurality of spatially defined and separated cell channels.

14. The microfluidic device according to claim 1, wherein said substrate is transparent for imaging and said plurality of spatially defined and separated cell channels have a dimension to accommodate cells in monolayer.

* * * * *

UNITED STATES PATENT AND TRADEMARK OFFICE
CERTIFICATE OF CORRECTION

PATENT NO. : 10,041,104 B2
APPLICATION NO. : 15/323357
DATED : August 7, 2018
INVENTOR(S) : Johan Elf et al.

Page 1 of 1

It is certified that error appears in the above-identified patent and that said Letters Patent is hereby corrected as shown below:

On the Title Page

Item "(30) Foreign Application Priority Data", change "1450860" to --1450860-0--.

Signed and Sealed this
Sixth Day of November, 2018

Andrei Iancu
*Director of the United States Patent and Trademark Office*